(12) United States Patent
Long et al.

(10) Patent No.: US 8,974,458 B2
(45) Date of Patent: Mar. 10, 2015

(54) ARTHROPLASTY INSTRUMENTS AND ASSOCIATED METHOD

(71) Applicant: DePuy Synthes Products, LLC, Raynham, MA (US)

(72) Inventors: Jack F. Long, Warsaw, IN (US); Joseph P. Iannotti, Maryfield Heights, OH (US); Gerald R. Williams, Jr., Villanova, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/749,969

(22) Filed: Jan. 25, 2013

(65) Prior Publication Data

US 2013/0138109 A1    May 30, 2013

Related U.S. Application Data

(62) Division of application No. 10/403,710, filed on Mar. 31, 2003, now Pat. No. 8,366,713.

(51) Int. Cl.
*A61B 17/00* (2006.01)
*A61B 17/16* (2006.01)
(Continued)

(52) U.S. Cl.
CPC ............. *A61B 17/16* (2013.01); *A61B 17/1684* (2013.01); *A61F 2/30734* (2013.01); *A61F 2/4612* (2013.01); *A61F 2/4657* (2013.01); *A61F 2/4684* (2013.01); *A61B 17/162* (2013.01); *A61B 2019/461* (2013.01); *A61F 2/30767* (2013.01); *A61F 2/30771* (2013.01);
(Continued)

(58) Field of Classification Search
USPC ................... 606/86 R, 79–81; 408/204, 206
See application file for complete search history.

(56) References Cited

U.S. PATENT DOCUMENTS 788,362 A    4/1905    Lavery
1,023,542 A    4/1912    Winter
(Continued)

FOREIGN PATENT DOCUMENTS

DE    2041929    8/1970
DE    4228710 A1    8/1992
(Continued)

OTHER PUBLICATIONS

Australian Examiners' Report corresponding to Australian Application No. 2009213073, mailed Feb. 25, 2011 (2 pages).
(Continued)

*Primary Examiner* — Kevin T Truong
*Assistant Examiner* — Michael Araj
(74) *Attorney, Agent, or Firm* — Maginot, Moore & Beck, LLP

(57) ABSTRACT

A reamer for use in performing arthroplasty includes a first cutting structure having an inner concave surface that defines a first cavity and terminates in a generally circular leading edge. The inner concave surface includes a first cutting feature that is spaced apart from the leading edge. An elongate member extends from the first cutting structure into the first cavity toward the leading edge that includes a second cutting feature. A second cutting structure is secured to the elongate member and positioned within the first cavity. The second cutting structure extends outwardly from the elongate member toward the inner concave surface and includes a third cutting feature.

18 Claims, 38 Drawing Sheets

(51) Int. Cl.
  *A61F 2/30* (2006.01)
  *A61F 2/46* (2006.01)
  *A61B 19/00* (2006.01)
  *A61F 2/40* (2006.01)

(52) U.S. Cl.
  CPC .................. *A61F2002/30214* (2013.01); *A61F 2002/30332* (2013.01); *A61F 2002/30341* (2013.01); *A61F 2002/30405* (2013.01); *A61F 2002/30433* (2013.01); *A61F 2002/30616* (2013.01); *A61F 2002/30736* (2013.01); *A61F 2002/30769* (2013.01); *A61F 2002/30777* (2013.01); *A61F 2002/30797* (2013.01); *A61F 2002/30808* (2013.01); *A61F 2002/30878* (2013.01); *A61F 2002/4007* (2013.01); *A61F 2002/4658* (2013.01); *A61F 2220/0025* (2013.01); *A61F 2220/0033* (2013.01); *A61F 2220/0041* (2013.01); *A61F 2230/0067* (2013.01); *A61F 2310/00017* (2013.01); *A61F 2310/00023* (2013.01); *A61F 2310/00029* (2013.01)
  USPC ............................................................. 606/80

(56) References Cited

U.S. PATENT DOCUMENTS

| | | | |
|---|---|---|---|
| 1,345,443 | A | 7/1920 | Hood |
| 1,669,701 | A | 5/1928 | Estwing |
| 2,200,120 | A | 5/1940 | Nauth |
| 2,222,517 | A | 11/1940 | Price |
| 2,243,718 | A | 5/1941 | Moreira |
| 2,718,228 | A | 9/1955 | Van Steenbrugghe |
| 2,725,878 | A | 12/1955 | Reiter |
| 2,804,895 | A * | 9/1957 | Clement ..................... 408/72 R |
| 2,934,065 | A | 4/1960 | Townley |
| 3,002,514 | A | 10/1961 | Deyerle |
| 3,605,527 | A * | 9/1971 | Gambale ......................... 76/115 |
| 3,702,611 | A | 11/1972 | Fishbein |
| 3,840,904 | A | 10/1974 | Tronzo |
| 3,855,638 | A | 12/1974 | Pilliar |
| 3,979,778 | A | 9/1976 | Stroot |
| 4,042,980 | A | 8/1977 | Swanson et al. |
| 4,206,517 | A | 6/1980 | Pappas et al. |
| 4,271,849 | A | 6/1981 | Rehder |
| 4,274,164 | A | 6/1981 | Rehder et al. |
| 4,328,593 | A | 5/1982 | Sutter et al. |
| 4,332,036 | A * | 6/1982 | Sutter et al. ................ 623/23.42 |
| 4,335,429 | A | 6/1982 | Kawakatsu |
| 4,355,429 | A | 10/1982 | Mittelmeier et al. |
| 4,432,358 | A | 2/1984 | Fixel |
| 4,441,492 | A | 4/1984 | Rydell et al. |
| 4,502,474 | A | 3/1985 | Comparetto |
| 4,550,450 | A | 11/1985 | Kinnett |
| 4,601,289 | A | 7/1986 | Chiarizzio et al. |
| 4,714,471 | A | 12/1987 | Grundei |
| 4,722,330 | A | 2/1988 | Russell et al. |
| 4,752,296 | A | 6/1988 | Buechel et al. |
| 4,787,378 | A | 11/1988 | Sodhi |
| 4,795,473 | A | 1/1989 | Grimes |
| 4,801,289 | A | 1/1989 | Sugimoto et al. |
| 4,805,607 | A | 2/1989 | Engelhardt et al. |
| 4,846,841 | A | 7/1989 | Oh |
| 4,865,605 | A | 9/1989 | Dines et al. |
| 4,865,609 | A | 9/1989 | Roche |
| 4,893,619 | A | 1/1990 | Dale et al. |
| 4,919,669 | A | 4/1990 | Lannelongue |
| 4,987,904 | A | 1/1991 | Wilson |
| 4,995,883 | A | 2/1991 | Demane et al. |
| 5,041,117 | A | 8/1991 | Engelhardt |
| 5,064,427 | A | 11/1991 | Burkinshaw |
| 5,070,623 | A | 12/1991 | Barnes |
| 5,108,396 | A | 4/1992 | Lackey et al. |
| 5,116,339 | A | 5/1992 | Glock |
| 5,141,520 | A | 8/1992 | Goble et al. |
| 5,226,915 | A | 7/1993 | Bertin |
| 5,250,051 | A | 10/1993 | Maryan |
| 5,258,033 | A | 11/1993 | Lawes et al. |
| 5,282,865 | A | 2/1994 | Dong |
| 5,312,411 | A | 5/1994 | Steele et al. |
| 5,314,479 | A | 5/1994 | Rockwood, Jr. et al. |
| 5,358,525 | A | 10/1994 | Fox et al. |
| 5,374,269 | A | 12/1994 | Rosenberg |
| 5,405,349 | A | 4/1995 | Burkinshaw et al. |
| 5,423,827 | A | 6/1995 | Mumme et al. |
| 5,454,816 | A | 10/1995 | Ashby |
| 5,470,336 | A | 11/1995 | Ling et al. |
| 5,476,467 | A | 12/1995 | Benoist |
| 5,486,178 | A | 1/1996 | Hodge |
| 5,490,852 | A | 2/1996 | Azer et al. |
| 5,507,817 | A | 4/1996 | Craig et al. |
| 5,514,139 | A | 5/1996 | Goldstein et al. |
| 5,540,696 | A | 7/1996 | Booth, Jr. et al. |
| 5,549,704 | A * | 8/1996 | Sutter ......................... 623/23.13 |
| 5,569,263 | A | 10/1996 | Hein |
| 5,662,476 | A | 9/1997 | Ingber et al. |
| 5,683,395 | A | 11/1997 | Mikhail |
| 5,690,636 | A | 11/1997 | Wildgoose et al. |
| 5,702,460 | A | 12/1997 | Carls et al. |
| 5,723,018 | A | 3/1998 | Cyprien et al. |
| 5,735,905 | A | 4/1998 | Parr |
| 5,769,852 | A | 6/1998 | Branemark |
| 5,776,194 | A | 7/1998 | Mikol et al. |
| 5,776,201 | A | 7/1998 | Colleran et al. |
| 5,779,710 | A | 7/1998 | Matsen, III |
| 5,800,437 | A | 9/1998 | Gustilo et al. |
| 5,800,557 | A | 9/1998 | Elhami |
| 5,830,216 | A | 11/1998 | Insall et al. |
| 5,893,850 | A | 4/1999 | Cachia |
| 5,957,926 | A | 9/1999 | Masini |
| 6,013,104 | A | 1/2000 | Kampner |
| 6,045,302 | A * | 4/2000 | Orr .................................. 408/83 |
| 6,045,582 | A | 4/2000 | Prybyla |
| 6,063,124 | A * | 5/2000 | Amstutz ..................... 623/22.21 |
| 6,071,311 | A | 6/2000 | O'Neil et al. |
| 6,093,124 | A | 7/2000 | Eyley |
| 6,102,916 | A | 8/2000 | Masini |
| 6,110,200 | A | 8/2000 | Hinnenkamp |
| 6,127,596 | A | 10/2000 | Brown et al. |
| 6,129,764 | A | 10/2000 | Servidio |
| 6,132,469 | A | 10/2000 | Schroeder |
| 6,156,069 | A | 12/2000 | Amstutz |
| 6,168,628 | B1 | 1/2001 | Huebner |
| 6,187,012 | B1 | 2/2001 | Masini |
| 6,190,390 | B1 | 2/2001 | McAllister |
| 6,200,319 | B1 | 3/2001 | Storer et al. |
| 6,206,884 | B1 | 3/2001 | Masini |
| 6,283,999 | B1 | 9/2001 | Rockwood, Jr. |
| 6,319,104 | B1 | 11/2001 | Emter |
| 6,334,874 | B1 | 1/2002 | Tornier et al. |
| 6,364,910 | B1 | 4/2002 | Shultz et al. |
| 6,368,353 | B1 | 4/2002 | Arcand |
| 6,508,840 | B1 | 1/2003 | Rockwood, Jr. et al. |
| 6,508,841 | B2 * | 1/2003 | Martin et al. ............... 623/23.12 |
| 6,554,865 | B2 | 4/2003 | Grusin et al. |
| 6,620,197 | B2 | 9/2003 | Maroney et al. |
| 6,709,439 | B2 | 3/2004 | Rogers et al. |
| 6,740,120 | B1 | 5/2004 | Grimes |
| 6,755,865 | B2 | 6/2004 | Tarabishy |
| 6,783,549 | B1 | 8/2004 | Stone et al. |
| 6,875,222 | B2 | 4/2005 | Long et al. |
| 6,942,699 | B2 | 9/2005 | Stone et al. |
| 6,979,299 | B2 | 12/2005 | Peabody et al. |
| 7,097,397 | B2 | 8/2006 | Keightley |
| 7,112,204 | B2 | 9/2006 | Justin et al. |
| 7,338,498 | B2 | 3/2008 | Long et al. |
| 7,517,364 | B2 | 4/2009 | Long et al. |
| 7,527,631 | B2 | 5/2009 | Maroney et al. |
| 7,670,382 | B2 | 3/2010 | Parrott et al. |
| 8,211,113 | B2 | 7/2012 | Brown et al. |
| 8,366,713 | B2 | 2/2013 | Long et al. |
| 8,444,646 | B2 | 5/2013 | Long et al. |
| 2001/0009971 | A1 | 7/2001 | Sherts et al. |

(56) References Cited

U.S. PATENT DOCUMENTS

| | | |
|---|---|---|
| 2001/0013823 A1 | 8/2001 | Hatakeyama et al. |
| 2001/0037152 A1 | 11/2001 | Rockwood, Jr. |
| 2001/0047210 A1 | 11/2001 | Wolf |
| 2002/0016634 A1 | 2/2002 | Maroney et al. |
| 2002/0099381 A1 | 7/2002 | Maroney et al. |
| 2002/0099445 A1 | 7/2002 | Maroney et al. |
| 2002/0133153 A1 | 9/2002 | Hyde, Jr. |
| 2002/0183849 A1 | 12/2002 | Grusin et al. |
| 2003/0018341 A1 | 1/2003 | Deloge et al. |
| 2003/0114859 A1 | 6/2003 | Grusin et al. |
| 2003/0163202 A1 | 8/2003 | Lakin |
| 2003/0212403 A1 | 11/2003 | Swanson |
| 2004/0122521 A1 | 6/2004 | Lee et al. |
| 2004/0193277 A1 | 9/2004 | Long et al. |
| 2004/0193278 A1 | 9/2004 | Maroney et al. |
| 2005/0065612 A1 | 3/2005 | Winslow |
| 2006/0052791 A1 | 3/2006 | Hagen et al. |
| 2006/0142870 A1 | 6/2006 | Robinson et al. |
| 2006/0149390 A1 | 7/2006 | Long et al. |
| 2008/0004701 A1 | 1/2008 | Axelson et al. |
| 2013/0245776 A1 | 9/2013 | Long et al. |

FOREIGN PATENT DOCUMENTS

| | | | |
|---|---|---|---|
| DE | 4220217 | A1 | 12/1993 |
| DE | 10233204 | A1 | 7/2002 |
| DE | 10233201 | A1 | 2/2004 |
| EP | 0845250 | A2 | 11/1997 |
| EP | 0888752 | A2 | 7/1998 |
| EP | 0903128 | A1 | 9/1998 |
| EP | 1064890 | A1 | 6/2000 |
| EP | 1228739 | | 8/2002 |
| EP | 1 470 802 | A1 | 10/2004 |
| EP | 1518519 | | 3/2005 |
| FR | 2418664 | | 3/1978 |
| FR | 2 418 644 | | 9/1979 |
| FR | 2578739 | | 9/1986 |
| FR | 2737107 | A1 | 7/1995 |
| FR | 2 737 107 | | 1/1997 |
| FR | 2898267 | A | 9/2007 |
| GB | 764600 | | 12/1956 |
| GB | 2259253 | A | 8/1992 |
| WO | 94/15551 | | 7/1994 |
| WO | 95/22302 | | 8/1995 |
| WO | 98/07393 | | 2/1998 |
| WO | 99/37254 | | 7/1999 |
| WO | 01/13823 | A2 | 3/2001 |
| WO | 02/17822 | A1 | 3/2002 |

OTHER PUBLICATIONS

European Search Report corresponding to European Application No. 04251913.2, mailed Dec. 5, 2005 (3 pages).

European Search Report for European Application No. 04251871.2-1526, Sep. 8, 2004 (3 pages).

European Search Report for European Application No. 05251328.0/2310, Jul. 21, 2005 (4 pages).

Biomet Orthopaedics, Inc., Introducing the Copeland Humeral Resurfacing Head, 2001.

Biomet Merck, Ltd., Copeland Surface Replacement Shoulder Arthroplasty, Dec. 10, 2003.

Endotec, Inc., Buechel-Pappas Resurfacing Shoulder System Surgical Procedure by Frederick F. Buechel, M.D. 2001.

Biomet Orthopaedics, Inc., Copeland Humeral Resurfacing Head, Dec. 10, 2003.

Biomet Brochure (engineering drawings) Dec. 17, 2009.

DePuy Orthopaedics, Inc., Global Advantage CTA Humeral Head, 2000, 6 pages, 3.5M0406, 0612-03-050 (Rev3), USA. Dec. 17, 2009.

EPO Search Report for EPO Application No. 04251913.2-2310, Dec. 5, 2005 (2 pages).

European Search Report in corresponding European application (i.e., EP10 18 7319), mailed Jan. 13, 2011, (8 pages).

DePuy Orthopaedics, Inc., Moreland Cemented Hip Revision Instrumentation, (12 pages total), 2.3M500, 0602-28-000 (Rev.6) USA, Jan. 5, 2010.

DePuy Orthopaedics, Inc., Moreland Cementless Hip Revision Instrumentation, (12 pages total), USA. Jan. 5, 2010.

Smith & Nefphew, Inc., Orthopaedic Catalog (25 pages total) prepared Oct. 16, 2003, USA.

DePuy Ace, Engineering Drawings, title: Articulated Tension Device Outline Drawings-Large Fragment System, P/N. 13710-010, Dec. 11, 1998 (Rev. C) USA.

Japan Patent Office, Notification of Reasons for Refusal, corresponding to Japanese patent application No. 2004-099913, dated Feb. 9, 2010 (3 pages).

Australian Government, IP Australia, Examiner's First Report on Australian patent application No. 2004201199, dated Jan. 9, 2009 (2 pages).

Australian Government—IP Australia, Examiner's First Report on Australian patent application No. 2004201349, dated Jun. 4, 2009 (7 pages).

* cited by examiner

FIG. 27 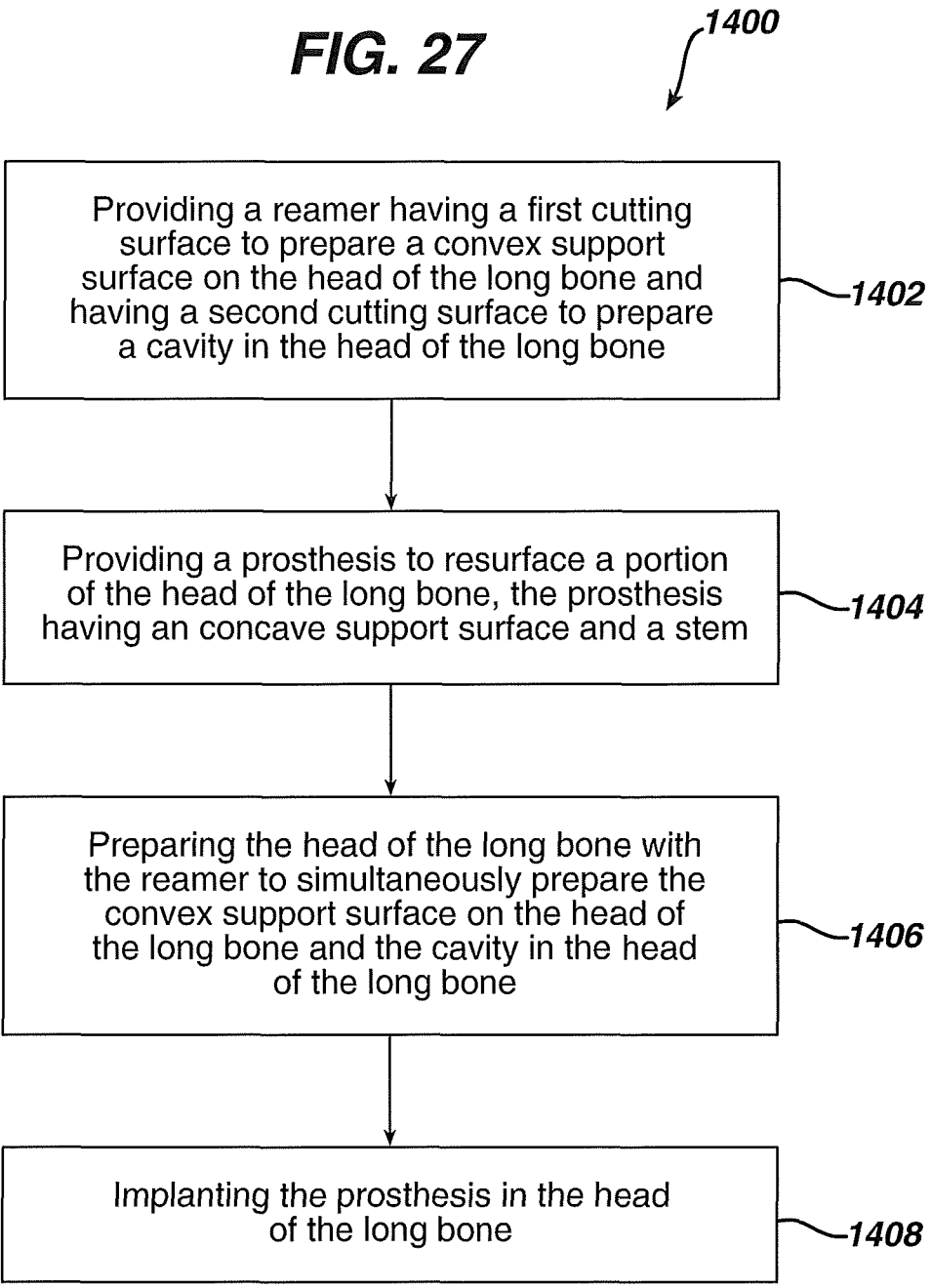

```
┌─────────────────────────────────────┐
│ Providing a reamer having a first   │
│ cutting surface to prepare a convex │
│ support surface on the head of the  │──1402
│ long bone and having a second       │
│ cutting surface to prepare a cavity │
│ in the head of the long bone        │
└─────────────────────────────────────┘
                  │
                  ▼
┌─────────────────────────────────────┐
│ Providing a prosthesis to resurface │
│ a portion of the head of the long   │
│ bone, the prosthesis having an      │──1404
│ concave support surface and a stem  │
└─────────────────────────────────────┘
                  │
                  ▼
┌─────────────────────────────────────┐
│ Preparing the head of the long bone │
│ with the reamer to simultaneously   │
│ prepare the convex support surface  │
│ on the head of the long bone and    │──1406
│ the cavity in the head of the long  │
│ bone                                │
└─────────────────────────────────────┘
                  │
                  ▼
┌─────────────────────────────────────┐
│ Implanting the prosthesis in the    │
│ head of the long bone               │──1408
└─────────────────────────────────────┘
```

ARTHROPLASTY INSTRUMENTS AND ASSOCIATED METHOD

CROSS-REFERENCE TO RELATED APPLICATIONS

This is a divisional application of U.S. patent application Ser. No. 10/403,710 entitled "Arthroplasty instruments and associated method" filed Mar. 31, 2003 (now U.S. Pat. No. 8,366,713 issued Feb. 5, 2013), the disclosure of which is hereby incorporated by reference herein in its entirety. Cross reference is also made to the following applications: Ser. No. 10/403,707 entitled "ARTHROPLASTY SIZING GAUGE" (now U.S. Pat. No. 7,527,631 issued May 5, 2009), Ser. No. 10/403,750 entitled "ARTICULATING SURFACE REPLACEMENT PROSTHESIS" (now Abandoned), Ser. No. 10/403,577 entitled "MODULAR ARTICULATING SURFACE REPLACEMENT PROSTHESIS" (now Abandoned), Ser. No. 10/403,708 entitled "EXTENDED ARTICULATION ORTHOPAEDIC IMPLANT AND ASSOCIATED METHOD" (now U.S. Pat. No. 7,517,364 issued Apr. 14, 2009), and Ser. No. 10/403,365 entitled "PROSTHETIC IMPLANT, TRIAL AND ASSOCIATED METHOD" (now U.S. Pat. No. 7,526,527 issued Apr. 28, 2009), which were each filed Mar. 31, 2003 and the disclosures of which are hereby incorporated by reference herein in their entirety.

TECHNICAL FIELD

The present disclosure relates generally to the field of orthopaedics, and more particularly, to implants and instruments for use in arthroplasty.

BACKGROUND

There are known to exist many designs and methods for implanting implantable articles, such as bone prostheses. Such bone prostheses include components of artificial joints, such as elbows, hips, knees and shoulders. An important consideration in the design and implanting of virtually any implantable bone prosthesis is that the bone have adequate fixation when implanted within the body.

Earlier designs of implantable articles relied upon the use of cement, such as polymethylmethacrylate (PMMA) to anchor the implant. The use of such implants can have some advantages, such as providing a fixation that does not develop free play or does not lead to erosion of joining faces postoperatively. However, the current trend is to use the cements to a lesser extent because of their tendency to lose adhesive properties over time and the possibility that cement contributes to wear debris within a joint.

Recently, implantable bone prostheses have been designed such that they encourage the growth of hard bone tissue around the implant. Such implants are often implanted without cement and the bone grows around surface irregularities, for example, porous structures on the implant.

One such implantable prosthesis is a shoulder prosthesis. During the lifetime of a patient, it may be necessary to replace the natural humeral head and associated glenoid cavity with a prosthesis. Such a shoulder replacement procedure may be necessary to be performed on a patient as a result of, for example, disease or trauma, for example, disease from osteoarthritis or rheumatoid arthritis.

Most shoulder replacement surgeries today involve the implantation of a total shoulder prosthesis. In a total shoulder replacement procedure, a humeral component having a head portion is utilized to replace the natural head portion of the upper arm bone or humerus. The humeral component typically has an elongated intramedullary stem which is utilized to secure the humeral component to the patient's humerus. In such a total shoulder replacement procedure, the natural glenoid surface of the scapula is restructured or otherwise replaced with a glenoid component that provides a bearing surface for the head portion of the humeral component.

With the average age of patients requiring shoulder arthroplasty decreasing, orthopaedic implant manufacturers are developing "bone-sparing" implants for the initial treatment of degenerative arthritis. While bone-sparing implants for the treatment of hip and knee arthroplasty are becoming quite common, bone-sparing shoulder arthroplasty techniques and prostheses are also being developed.

Shoulder surface replacement prostheses are being developed to replace the articulating surface of the proximal humerus with a minimal bone resection and minimal disruption of the metaphysis and the diaphysis. Current designs use a semi-spherical articular dome with a small stem for rotational stability. The under surface of the articular head is also semi-spherical and meets with a spherically machined humeral head.

Typically, however, arthritis of the gleno-humeral joint causes flattening of the humeral head with a large medial osteophyte. The flat humeral head can cause voids in the bone under the prosthesis resulting in limited contact between the prosthesis and the resected bone and may limit the load transfer capability between the prosthesis and the humerus.

Referring now to FIG. 2, a healthy long bone or, in the form of, for example, a humerus 1 is shown. The humerus 1 includes a head 2 on the proximal end of the humerus 1. The head 2 of a healthy humerus has a arcuate outer periphery. The arcuate outer periphery is generally hemispherical and meets with a concave glenoid cavity 3.

Referring now to FIG. 3, a diseased humerus 4 is shown. The diseased humerus 4 includes a head 5. The head 5 is flattened as shown in FIG. 3. The humerus 4 also has developed a large medial osteophyte 7.

Referring now to FIG. 4, a prior art prosthesis 8 is shown in position on the head 5 of diseased humerus 4. The head 5 includes a flattened humeral head area or bony defect 9, which leads to a void 6 between the prosthesis 8 and the bony defect 9.

When preparing a humeral head for a bone sparing or conservative shoulder arthroplasty, the semi-spherical humeral head is prepared by, for example, a grater type hollow hemispherical grater-type reamer. Such reamers are available from, for example, Othy, Inc., 460 West 350 North, Warsaw, Ind. 46580.

Additional steps to prepare the humeral head to receive a conservative or bone sparing humeral prosthesis may be required. For example, the bone sparing or conservative humeral prosthesis may include a stem for anchoring the prosthesis into the humerus.

The humeral head needs to be prepared to receive the stem. Typically, a drill and/or a reamer may be required to prepare the prosthesis to receive the stem. Such drills and reamers add time to the surgical procedure as well as represent a problem with the reamer having an orientation off center or skewed with respect to the hemispherical portion of the prepared humerus.

Current resurfacing instrumentation, therefore, addresses bone preparation techniques separately or sequentially. This type of procedure increases time, cost and mistakes. Operating room time is increased because the surgeon and the operating room personnel are handling more instrumentation.

Cost is increased because more instruments need to be manufactured and processed. More mistakes can be made because more instruments are handled and consequently the greater is the chance of dropping or making the wrong instrument selection.

SUMMARY

According to the present disclosure, a humeral head cutting tool is provided that performs several precise cutting functions simultaneously. The cutting tool includes a concave cutting area which prepares a convex head portion for the humeral prosthesis. The cutting tool also includes a tapered cylindrical reamer, which extends from the concave portion of the reamer to provide for an opening to receive the stem of the conservative or bone sparing prosthetic implant for the humerus.

The present disclosure provides for a long bone head cutting tool that prepares the head of the long bone for receiving a trial in one operation that provides multiple cutting functions simultaneously.

According to one embodiment of the present disclosure, there is provided an instrument for use in performing arthroplasty. The instrument includes a first portion adapted to prepare a convex surface on the head of the long bone. The instrument also includes a second portion adapted to prepare an elongated cavity or a third portion adapted to prepare a central support surface on the head of the long bone, or both the second and third portions. The third portion and the second portion are operably associated with the first portion.

According to another embodiment of the present disclosure, there is provided a reamer for use in performing arthroplasty. The reamer includes a generally arcuate member having an inner concave surface and an outer convex surface adapted to prepare a convex surface on a bone. The arcuate member has an axis of rotation of the member. The reamer also includes a central member operably associated with the arcuate member. The central member is adapted for preparing a support surface. The central member has an axis of rotation of the central member. The reamer further includes a generally cylindrical member operably associated with the planar member or the arcuate plate, or both. The cylindrical member is adapted for preparing a generally cylindrical surface. The cylindrical member defines an axis of rotation of the cylindrical member.

According to a further embodiment of the present disclosure, there is provided a cutting tool assembly for use in performing arthroplasty. The cutting tool assembly includes a reamer. The reamer has a first portion adapted to prepare a convex surface, a second portion adapted to prepare an elongated cavity and a third portion adapted to prepare a central surface. The first portion, the second portion and the third portion are operably associated with each other. The cutting tool also includes a driver releasably securable to the reamer. The driver is adapted to be attachable to a power tool to rotate the reamer.

According to another embodiment of the present disclosure there is provided a method from performing arthroplasty on the head of a long bone. The method includes the steps of providing a reamer having a first cutting surface to prepare a convex support surface on the head of the long bone and having a second cutting surface to prepare a cavity in the head of the long bone, providing a prosthesis to resurface a portion of the head of the long bone, the prosthesis having a concave support surface and a stem, preparing the head of the long bone with the reamer to simultaneously prepare the convex support surface on the head of the long bone and the cavity in the head of the long bone and implanting the prosthesis in the head of the long bone.

The technical advantage of the present disclosure includes the ability to reduce the time to perform a shoulder arthroplasty. For example, according to one aspect of the present disclosure, a cutting tool is provided that prepares the head of a long bone for receiving a trial in one operation by performing multiple cutting functions simultaneously. The cutting tool may, for example, provide the forming or cutting of the convex humeral head as well as preparing the tapered opening to receive the stem. Both the humeral head contour and the trial opening are thus prepared simultaneously with one instrument. Thus, separate tapered reamers and hollow hemispherical grater-type reamers are not required. Thus, the present disclosure provides for reduced time in the operating room by reducing the amount of instrumentation that the surgeon and staff will need to handle during the operation.

Another advantage of the present disclosure includes reducing the cost associated with the instruments for an operation. For example, according to another aspect of the present disclosure, a long bone head shaper prepares the long bone head for trial seating in one operation by performing multiple cutting functions simultaneously. The cutting tool may include a concave grater-type reamer and a tapered cylindrical reamer all built into one cutting tool. This combination tool replaces two separate tools, and therefore reduces cost. Thus, the present disclosure provides for cost reduction of instrument sets.

Another technical advantage of the present disclosure includes the reduction of surgical errors. For example, according to one aspect of the present disclosure, a cutting tool is provided that prepares the head of a long bone for trial seating in one operation by performing multiple cutting functions simultaneously. The tool may be in the form of, for example, a hollow hemispherical grater-type reamer with a centrally located tapered cylindrical reamer. The hemispherical portion provides for a hemispherical head on the long bone and the tapered cylindrical portion provides for receiving the stem of the prosthesis. Since mistakes can be made because the more instruments the surgeons handle the greater chance of dropping and damaging the instruments or making the wrong instrument selection can occur. Thus, the present disclosure provides for reductions in the likelihood of surgical mistakes.

Another technical advantage of the present disclosure includes the ability to optimize the accuracy of the surfaces prepared for a conservative or bone conserving long bone head implant. For example, according to one aspect of the present disclosure, a long bone head cutting tool is provided that prepares the head of the long bone for trial or prosthesis seating in one operation by performing multiple cutting functions simultaneously. Since both the hemispherical head and the stem are prepared with the same tool simultaneously, the concentricity and alignment of the surfaces are optimized. Thus, the present disclosure provides for improved quality of the surfaces prepared for a prosthesis.

Other technical advantages of the present disclosure will be readily apparent to one skilled in the art from the following figures, descriptions and claims.

BRIEF DESCRIPTION OF THE DRAWINGS

For a more complete understanding of the present disclosure and the advantages thereof, reference is now made to the following description taken in connection with the accompanying drawings, in which:

FIG. 27 is a process flow chart for a method of performing shoulder arthroplasty according to another embodiment of the present disclosure.

DETAILED DESCRIPTION

Embodiments of the present invention and the advantages thereof are best understood by referring to the following descriptions and drawings, wherein like numerals are used for like and corresponding parts of the drawings.

Figure 1:
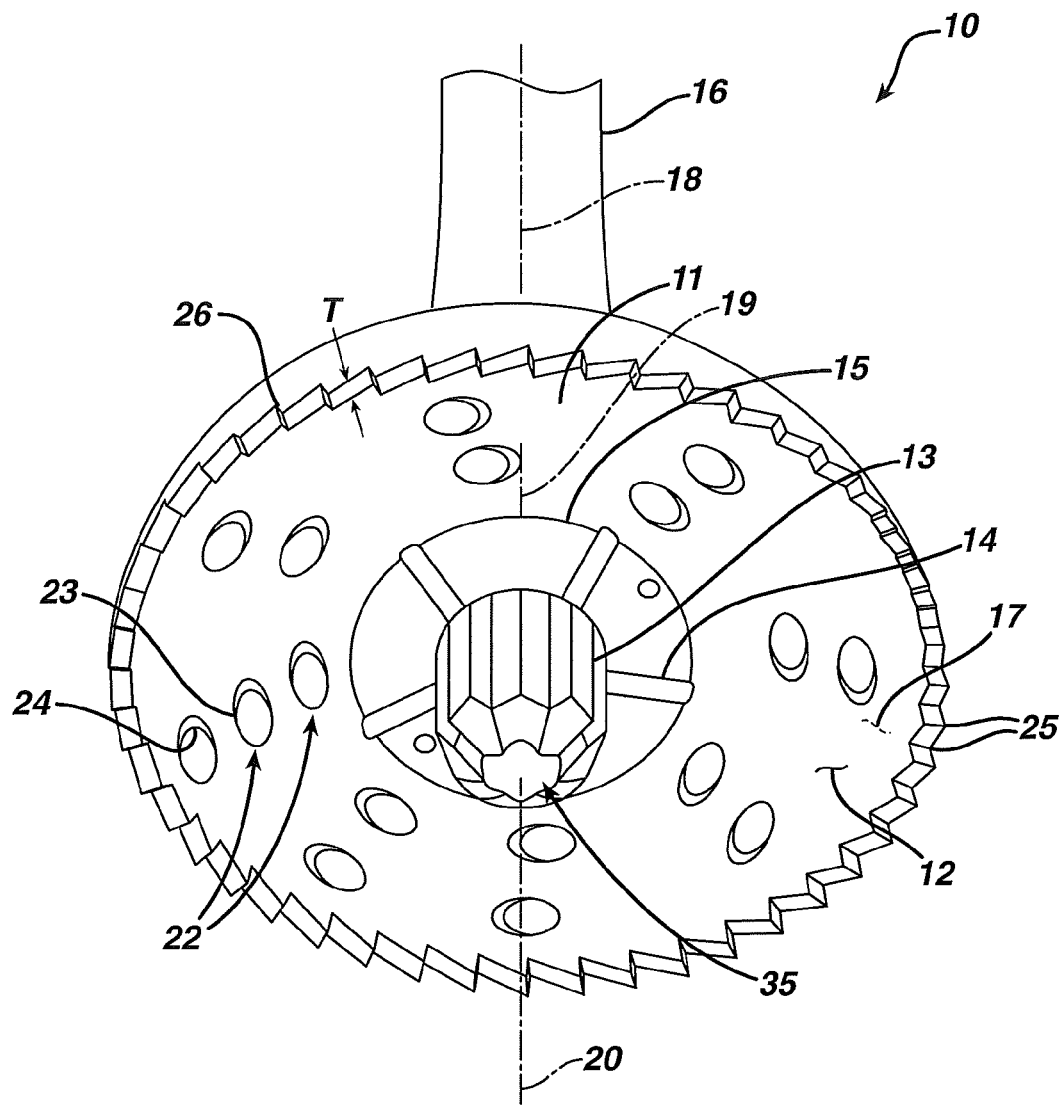
FIG. 1 is a perspective view of a reamer according to the present disclosure that may be used to prepare the humerus for a surface replacement prosthesis for use on a diseased humerus.
Figure 1A:
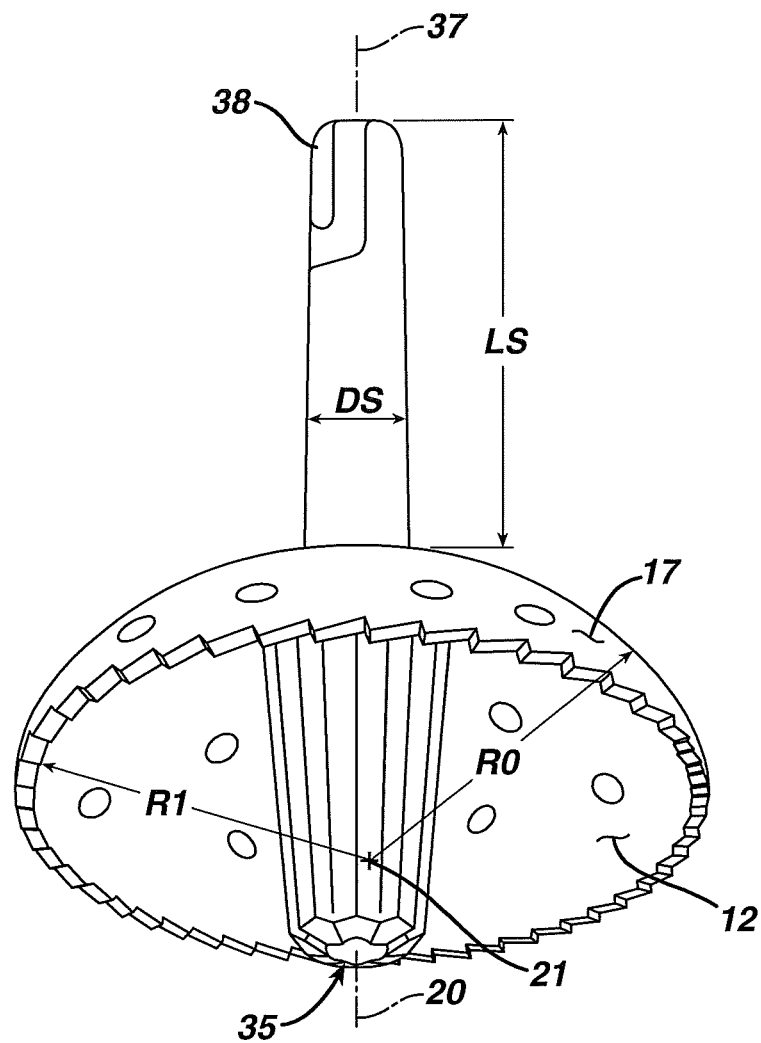
FIG. 1A is another perspective view of the reamer of FIG. 1.

Referring now to FIG. 1, an instrument 10 is shown according to the present invention. The instrument 10 is used for performing arthroplasty on a long bone. The instrument 10 includes a first portion 11 adapted to prepare a convex surface on a head of a long bone. The instrument 10 further includes a second portion 13 or a third portion 14. The instrument 10 may include both the second portion 13 and the third portion 14. The second portion 13 is adapted to prepare a cavity in the form of, for example, a trial hole 62 (see FIGS. 6 and 7) on the head 5 of a long bone 4. The third portion 14 is adapted to prepare a planar surface 56 on the head 5 of a long bone 4 (see FIGS. 6 and 7). As shown in FIGS. 1 and 1A, the first portion 11 comprises an arcuate disc-shaped body for forming a generally hemispherical contour 64 on the long bone 4 (see FIGS. 6 and 7).

Continuing to refer to FIGS. 1 and 1A, the instrument 10 may further include a fourth portion 16 extending from the first portion 11 in a direction opposed to the second portion 13. The fourth portion 16 is used for transferring torque to the instrument 10.

As shown in FIGS. 1 and 1A, the instrument 10 may be in the form of a reamer. The reamer may be used to perform arthroplasty on, for example, a head 4 of a humerus 3 (see FIGS. 6 and 7).

Referring again to FIGS. 1 and 1A, the reamer 10 may include the arcuate disc-shaped body or plate 15. The plate 15 may include the concave surface 12 and an outer convex surface 17. The plate 15 is adapted to prepare the convex surface 64 on the head 5 of the bone 4 (see FIGS. 6 and 7). The first portion 11 defines a first portion axis of rotation 18.

The third portion or planar member 14 is operably associated with the first portion 11. The portion 14 is adapted to prepare the planar portion or resected surface 56 of the head 4 of the bone 5 (see FIGS. 6 and 7). The planar member 14 defines an axis of rotation 19 of the planar portion 14.

The instrument 10 may also include the second portion 13 or cylindrical member which is associated with the planar member or the arcuate plate 11. The cylindrical member 13 is adapted to prepare the trial stem hole 62 of the head 5 of the bone 4 (see FIGS. 6 and 7). The cylindrical member 13 defines an axis of rotation 20 thereof.

Referring now to FIGS. 1 and 1A, the first portion 11 may be in the form of a hollow hemisphere defined by an inner radius RI extending from origin 21 defining concave surface 12 and an outer radius RO originating from origin 21 defining the outer convex surface 17. The distance between the concave surface 12 and the convex surface 17 may be defined by thickness T. The instrument 10 may include a concave surface cutting feature 22. The concave feature cutting feature may be any type of a cutting tool and may include, for example, a plurality of blades (not shown) or other types of cutting edges. For example, and as shown in FIGS. 1 and 1A, the concave surface 12 may include a plurality of spaced apart openings 23. The cutting feature 22 may be in the form of cutting surfaces formed on the edge 24 of the openings 23 formed in the concave surface 12.

Figure 1B:
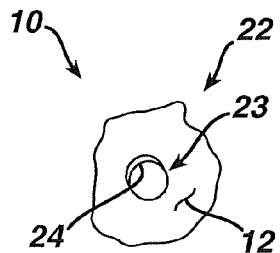
FIG. 1B is partial plan view of the reamer of FIG. 1 showing the openings in the body in greater detail.

Referring now to FIG. 1B, the cutting feature 22 and the form of edge 24 on the openings 23 are shown in greater detail.

Referring again to FIG. 1, the first portion 11 may also include a plurality of circumferential saw teeth 25 extending from the circular periphery 26 of the first portion 11. The teeth 25 serve to provide a proper seat for the prosthesis.

The instrument 10 including the first portion 11, second portion 13, third portion 14 and fourth portion 16, may be made of any suitable durable material and may, for example, be made of a durable plastic, a ceramic or a metal that is compatible with the human anatomy and which may be sterilized by a commercially available method. If made of a metal, the instrument 10 may be made of, for example, a titanium alloy, a cobalt chromium alloy, or a stainless steel alloy.

The first portion 11, if made of a metal, may be either formed, cast or machined from a solid.

Referring again to FIGS. 1 and 1A, the third portion or planar member 14 may, for example, be generally washer shaped.

Figure 1C:
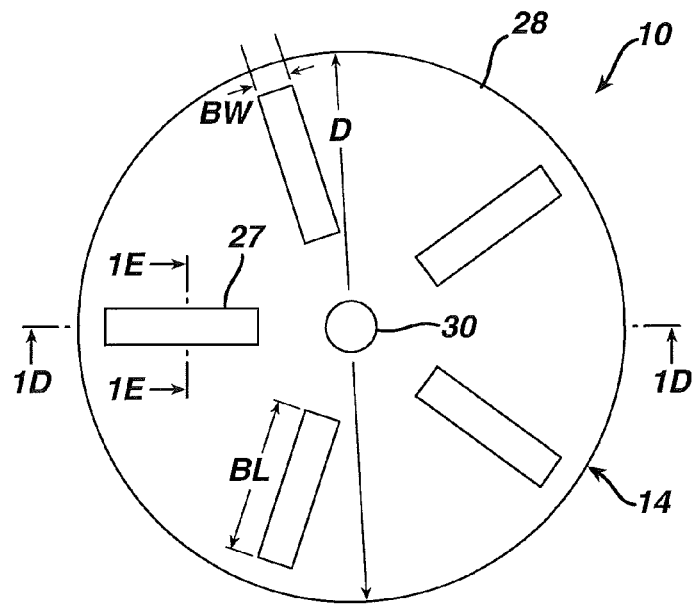
FIG. 1C is a partial bottom view of the reamer of FIG. 1 showing the planar cutting surface in greater detail.
Figure 1D:
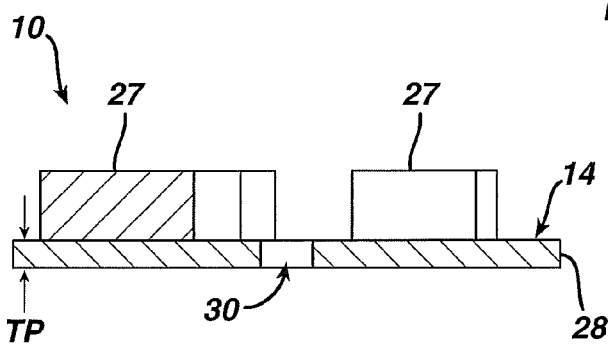
FIG. 1D is a partial plan view of the reamer of FIG. 1C along the line 1D-1D in the direction of the arrows.
Figure 1E:
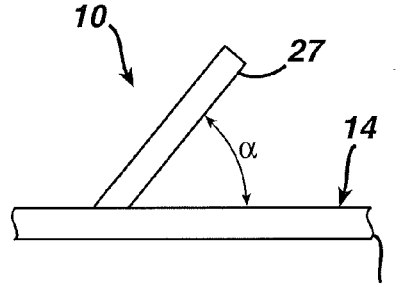
FIG. 1E is a partial plan view of the reamer of FIG. 1C along the line 1E-1E in the direction of the arrows.

Referring now to FIGS. 1C, 1D and 1E, the planar member 14 is shown in greater detail. The planar member 14 may, for example, be generally washer shaped having a diameter D and a thickness TP. The planar member 14 may include a plurality of spaced apart blades 27.

Referring to FIG. 1E, the blades 27 may extend from planar member body 28 at an angle, for example, of $\alpha$. $\alpha$ may be, for example, 15 to 55 degrees.

As shown in FIG. 1C, the plurality of blades 27 may be equally spaced. While there may be a solitary blade 27, a plurality of blades would even the cutting forces with a reasonable quantity of, for example, 3, 4, 5 or 6 blades being suggested. Five blades are shown in the planar member 14 of the instrument 10. The planar member 14 may include a central opening 30 to provide for a central cannulation or to receive the second portion 13.

The planar portion 14 may be manufactured by any suitable technique and may, for example, be made of a stamping, a casting or machined from solid stock.

Figure 1F:
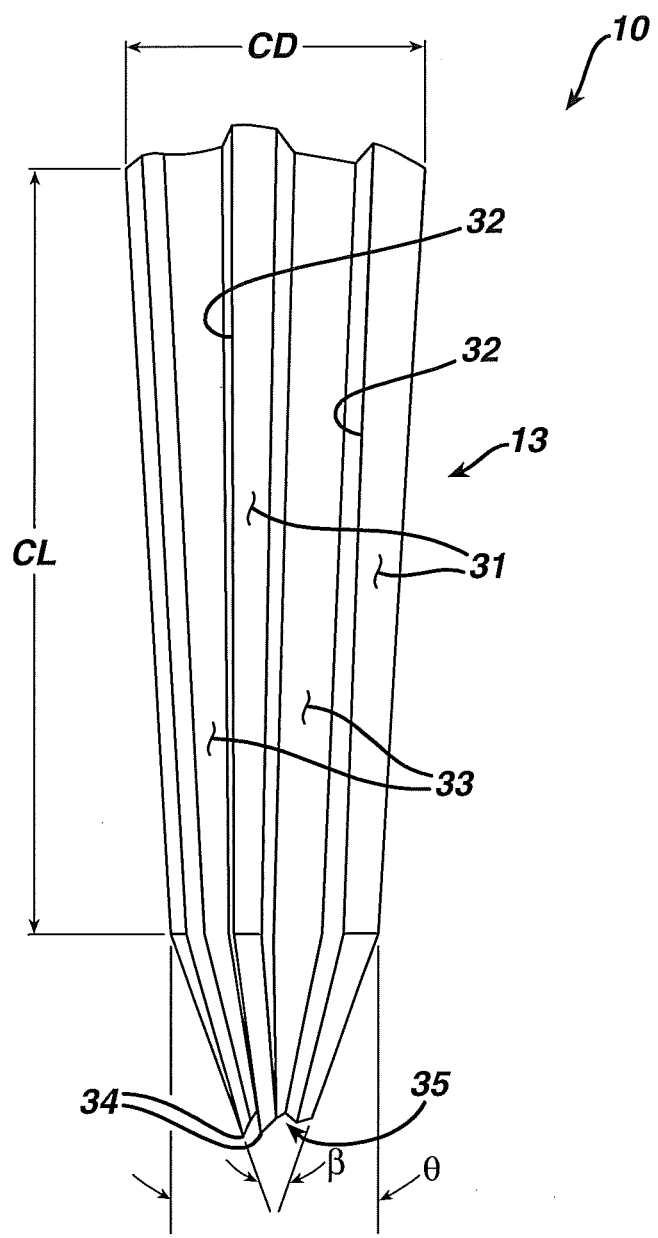
FIG. 1F is a partial plan view of the reamer of FIG. 1 showing the tapered cylindrical cutting surface in greater detail.

Referring now FIG. 1F, the tapered cylindrical member 13 is shown in greater detail. The tapered cylindrical member may include a plurality of lands or flutes 31. The lands 31 may includes a cutting edge 32. The cutting edges 32 may be equally spaced around the periphery of the cylindrical member 13.

The number of lands 31 may be any suitable number and may be, for example, 2, 3, 4, 5 or 6. The instrument 10 of the present invention shows 4 spaced apart lands. Separating each particular land 31 is a relief 33. The tapered cylindrical reamer may include a tapered cutting edge 34 defined by an included angle $\beta$. The cylindrical member 13 may include a central hole or cannulation 35. The hole or cannulation 35 may be used to assist in directing the instrument 10. The cylindrical member 13 may be defined by a diameter CD and a length CL.

The cylindrical reamer 13 may be made by any suitable technique and may, for example, be machined from solid stock or extruded. The cylindrical reamer 13 may have a tapered shape defined by angle $\theta$.

Referring again to FIGS. 1 and 1A, the shank 16 extends in a direction opposed to the cylindrical member 13. The shank 16 serves to provide a driving mechanism to rotate the instrument. The shank 10 may be generally cylindrical defined by a diameter DS and a length LS. The shank 16 may have a shank centerline 37, which is generally coincident with the cylindrical member's centerline 20. To assist in the quick removal of the instrument 10, the shank 37 may include a removal feature 38 in the form of, for example, a bayonet mounting as shown in FIG. 1A.

Referring now to FIGS. 1G through 1N, the first portion 11, the second portion 13, the third portion 14, and the fourth portion 16 of the instrument 10 may all be integral to each other or be made of separate components connected to each other. Any suitable method may be utilized to connect the portions 11, 13, 14 and 16 if they are separable components.

Figure 1G:
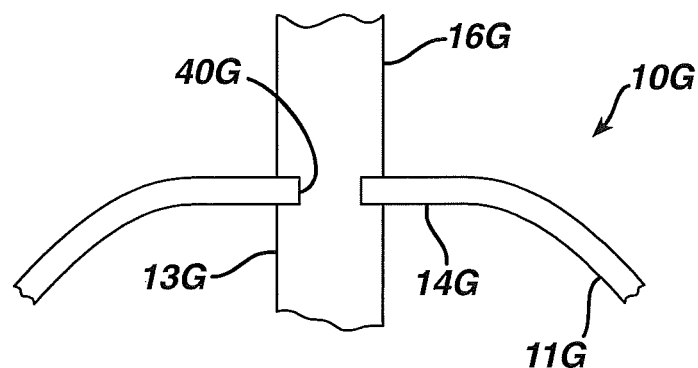
FIG. 1G is a partial plan view partially in cross section of another embodiment of the reamer of the present disclosure.
Figure 1H:
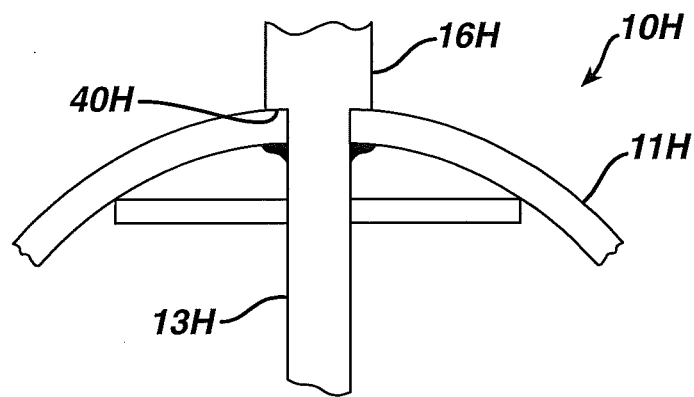
FIG. 1H is a partial plan view partially in cross section of yet another embodiment of the reamer of the present disclosure.

Referring now FIGS. 1G, 1H, 1J and 1K, the fourth portion, which is generally cylindrical, and the third portion which is generally cylindrical and which have generally the same centerline can very reasonably be integral with each other. For example, instrument 10G of FIG. 1G shows the fourth portion 16G being integral with the second portion 13G. Similarly, instrument 10H of FIG. 1H shows the fourth portion 16H being integral with the second portion 13H. Further referring to FIG. 1K, the instrument 10K shows the fourth portion 16K being integral with the second portion 13K.

Figure 1J:
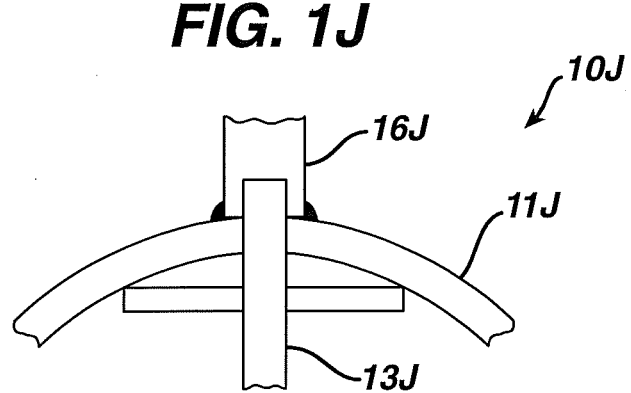
FIG. 1J is a partial plan view partially in cross section of another embodiment of the reamer of the present disclosure.

Referring now to FIG. 1J, the instrument 10J is shown with the fourth portion 16J and the second portion 13J being separable components. As shown in FIG. 1J, the fourth portion 16J and the second portion 13J are interferencely fit. It should be appreciated that the second portion 13J and fourth portion 16J may be welded, taper locked or threaded to each other, for example.

Referring now to FIGS. 1K, 1L, 1M and 1N, the third portion 14 may be secured to the first portion 11 in any suitable fashion. For example, referring to FIG. 1K, the third portion 14K of instrument 10K may be secured to the first portion 11K by means of welding between the outer periphery of the third portion 14K and the first portion 11K.

Figure 1K:
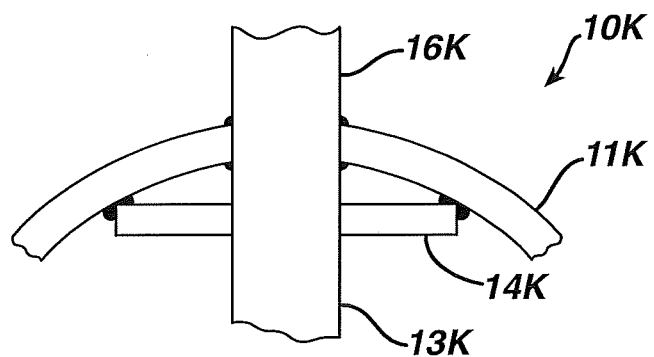
FIG. 1K is a partial plan view partially in cross section of another embodiment of the reamer of the present disclosure.
Figure 1L:
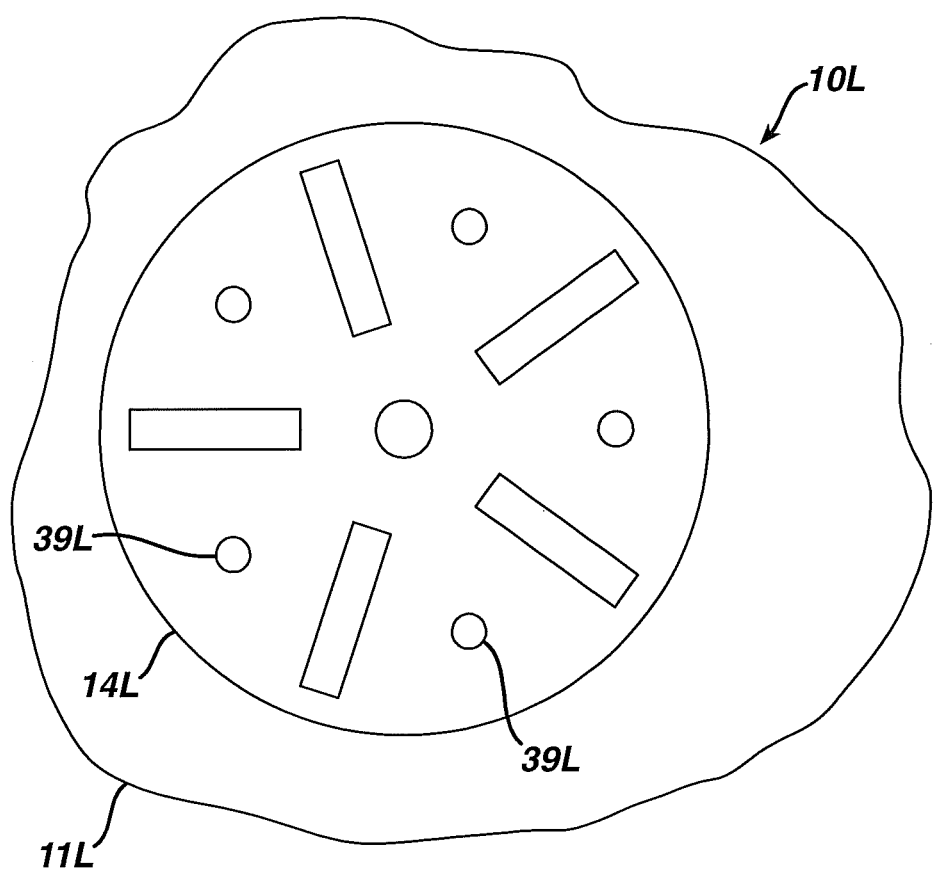
FIG. 1L is a partial bottom view of yet another embodiment of the reamer of the present disclosure.

Further referring now to the instrument 10L of FIG. 1L, the third portion 14L may be welded to the first portion 11L by a plurality of welds 39L located in a spaced-about position on the third portion 14L.

Figure 1M:
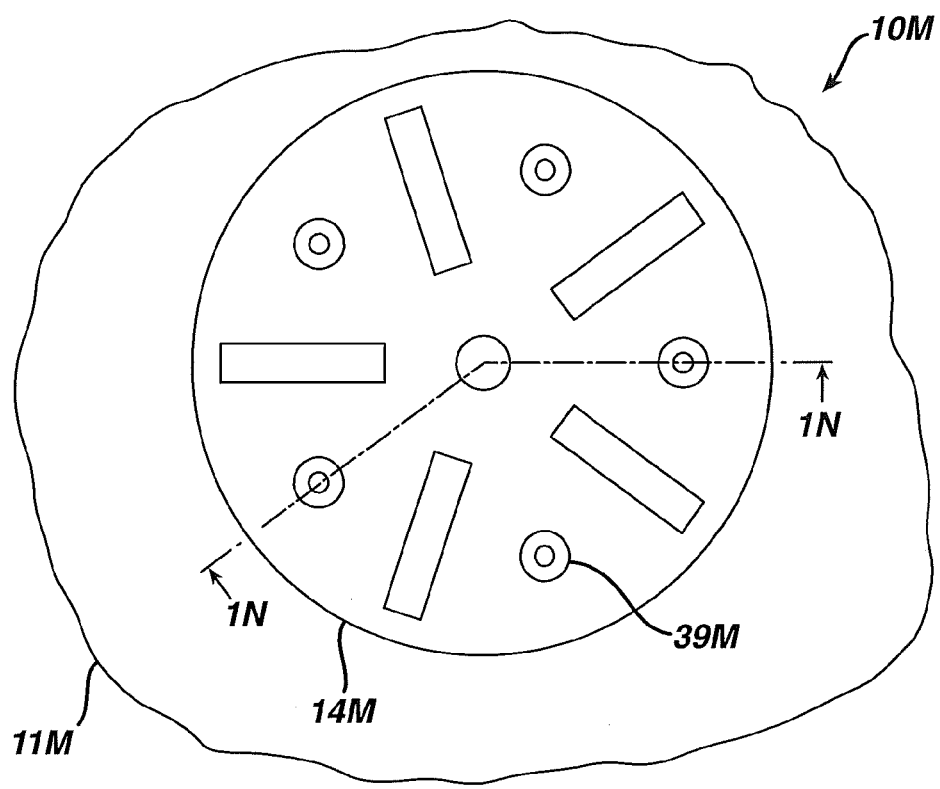
FIG. 1M is a partial bottom view of another embodiment of the reamer of the present disclosure.
Figure 1N:
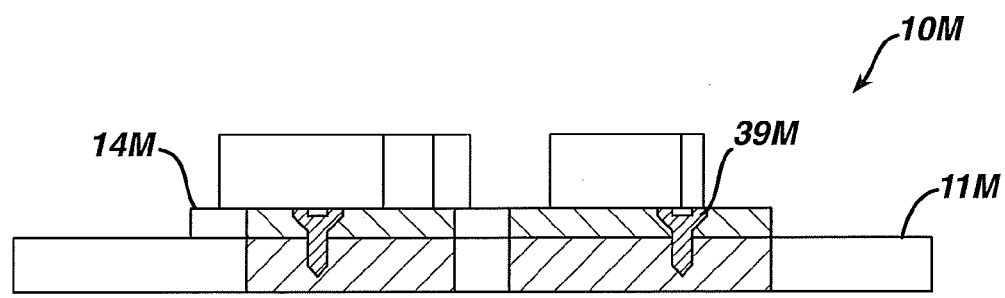
FIG. 1N is a partial cross-sectional view of the reamer of FIG. 1M along the line 1N-1N in the direction of the arrows.
Figure 1P:
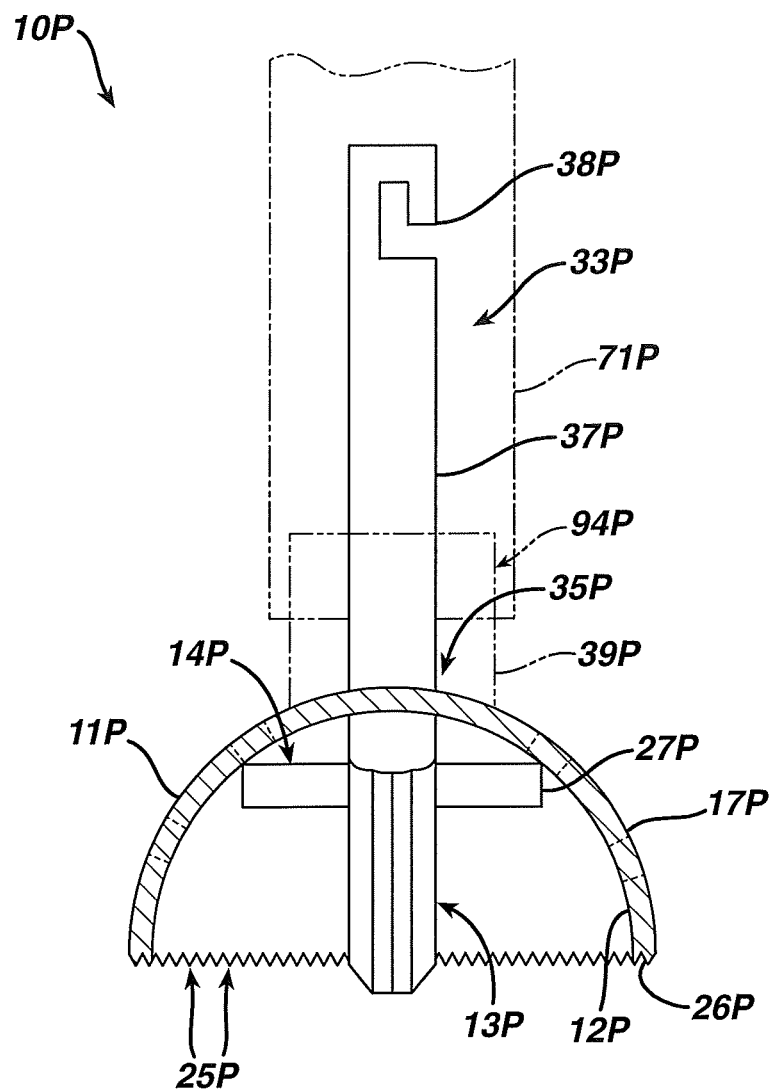
FIG. 1P is a plan view partially in cross section of another embodiment of the reamer of the present disclosure.

Referring now to instrument 10M of FIGS. 1M and 1N, the third portion 14M may be connected to the first portion 11M by means of a plurality spaced-apart fasteners in the form of, for example, threaded fasteners 39M. The fasteners 39M will secure the third portion 14M to the first portion 11M.

Referring now to FIGS. 1G, 1H, 1J, and 1K, it should be appreciated that the first portion 11 may be secured to the second portion 13 and the fourth portion 16 in any suitable manner. For example, referring to FIG. 1G, the second portion 13G and the fourth portion 16G may be integral and include a circumferential recess 40G into which the first portion 11G, that includes third portion 14G, may be snap-fitted.

Referring now to FIG. 1H, the second portion 13H may be integral with the fourth portion 16H and the portions 13H and 16H may include a shoulder 40H there between upon which the first portion 11H may be secured. It should be appreciated that the first portion 11H may be welded or interferencially fit to the second portion 13H.

Referring now to FIGS. 1J and 1K, the first portions 11J and 11K may be welded to the fourth portions 16J and 16K, respectively.

Referring now to FIGS. 1P-U, another embodiment of the present invention is shown as instrument 10P. The instrument 10P includes a first portion 11P, a second portion 13P and a third portion 14P. The first portion 11P and the second portion 13P may be similar to the first portion 11 and the second portion 13 of the instrument 10 of FIG. 1. The instrument 10P may also include a fourth portion 16P similar to fourth portion 16 of the instrument 10 of FIG. 1.

Figure 1Q:
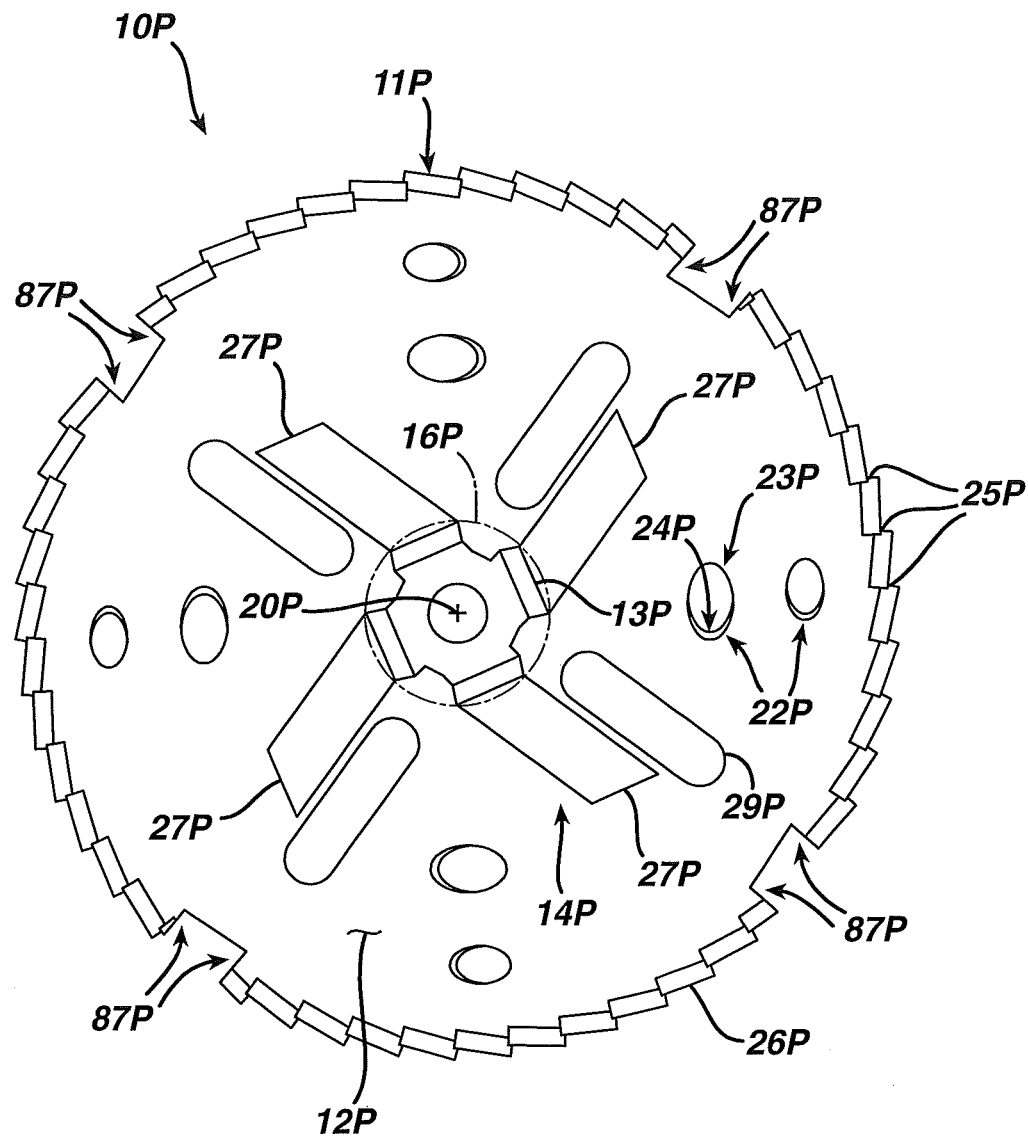
FIG. 1Q is a bottom view of the reamer of FIG. 1P.
Figure 1R:
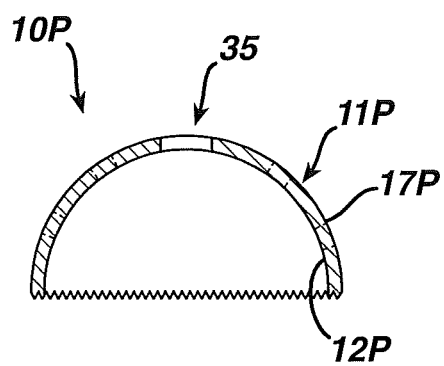
FIG. 1R is a plan view partially in cross section of the arcuate cutting portion of the reamer of FIG. 1P.
Figure 1T:
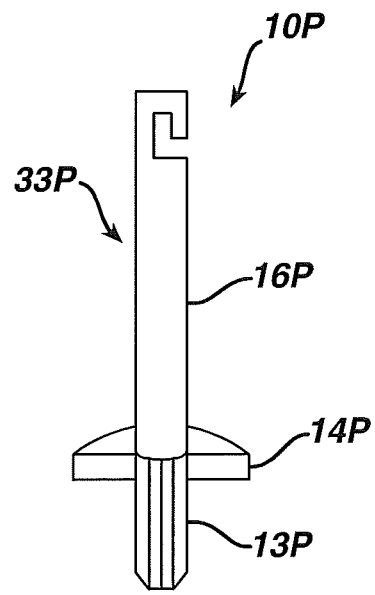
FIG. 1T is a plan view partially in cross section of the cylindrical and central cutting portion of the reamer portion of FIG. 1P.

The third portion 14P may be a separate component from the first portion 11P and the second portion 13P, or as shown in FIG. 1T, the third component 14P may be integral with the second portion 13P and the fourth portion 16P.

Referring now to FIG. 1Q the third portion 14P includes a blade 27P extending outwardly from the second portion 13P.

The third portion 14P may have a solitary blade 27P, or as shown in FIG. 1Q the blade 27P may have four equally spaced apart blades 27P.

The instrument 10P also includes the second portion or cylindrical member 13P that is integral with the third member 14P and the fourth member 16P. The cylindrical member 13P is adapted to prepare the trial stem hole 62A of the head 4 of the bone 3 (see FIGS. 6 and 7). The cylindrical member 13P defines an axis of rotation thereof.

Referring again to FIGS. 1P and 1Q, the first portion 11P may be in the form of a hollow hemisphere defining concave surface 12P and an outer convex surface 17P. The instrument 10P includes a concave surface cutting feature 22P in the form of cutting surfaces formed on edge 24P of openings 23P formed in the concave surface 12P (see FIG. 1Q). The first portion 11P may include through slots 29P to assist bone chip removal and sterilizing.

Referring again to FIG. 1P, the first portion 11P may also include a plurality of circumferential saw teeth 25P extending from the circular periphery 26P of the first portion 11P.

Figure 1S:
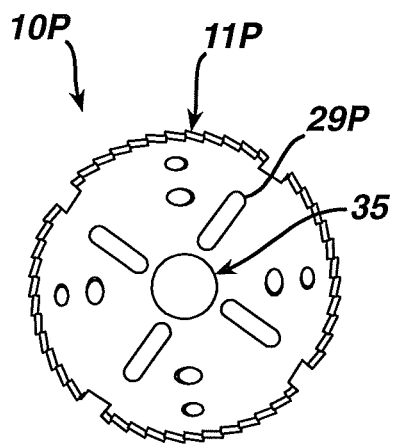
FIG. 1S is a bottom view of the arcuate cutting portion of FIG. 1P.

Referring now to FIGS. 1R and 1S the first portion 11P is shown as a separate component. As a separate component the first portion 11P can be easily sterilized.

Figure 1U:
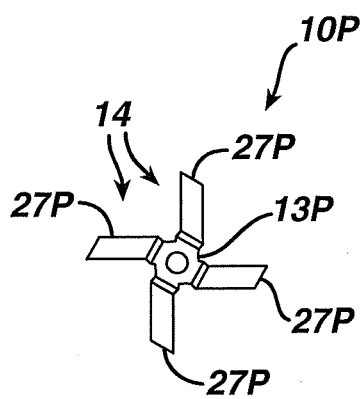
FIG. 1U is a bottom view of the cylindrical and central cutting portion of FIG. 1P.

Referring now to FIGS. 1T and 1U the second portion 13P, the third portion 14P, and the fourth portion 16P are shown as an integral reamer component 33P. As a separate component the integral reamer component 33P can be more easily sterilized.

Referring again to FIG. 1P the first portion 11P can be assembled onto the integral reamer component 33P with shaft 37P of the integral reamer component 33P fitting into the opening 35P of the first portion 11P. Threads 94P on the driver 71P (shown in phantom) and the collar 34P are used to move the collar of driver 71 P toward first portion 11P, trapping the first portion 11P between the collar and a convex portion of the third portion 14P.

The instrument 10P including the first portion 11P, second portion 13P, third portion 14P and fourth portion 16P, may be made of any suitable durable material and may, for example, be made of a durable plastic, a ceramic or a metal that is compatible with the human anatomy and which may be sterilized by a commercially available method. If made of a metal, the instrument 10P may be made of, for example, a titanium alloy, a cobalt chromium alloy, or a stainless steel alloy.

Figure 1V:
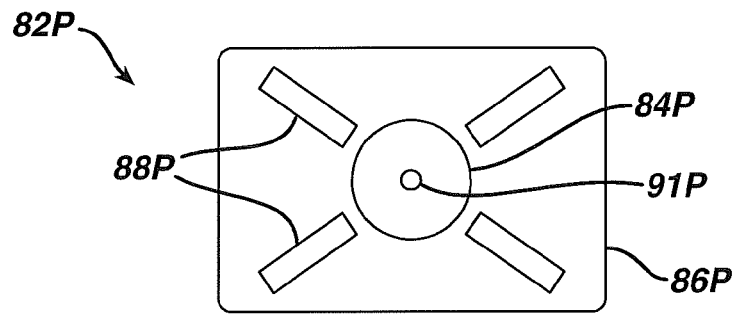
FIG. 1V is a plan view partially in cross section of a cutter removal tool for the reamer of FIG. 1P.
Figure 1W:
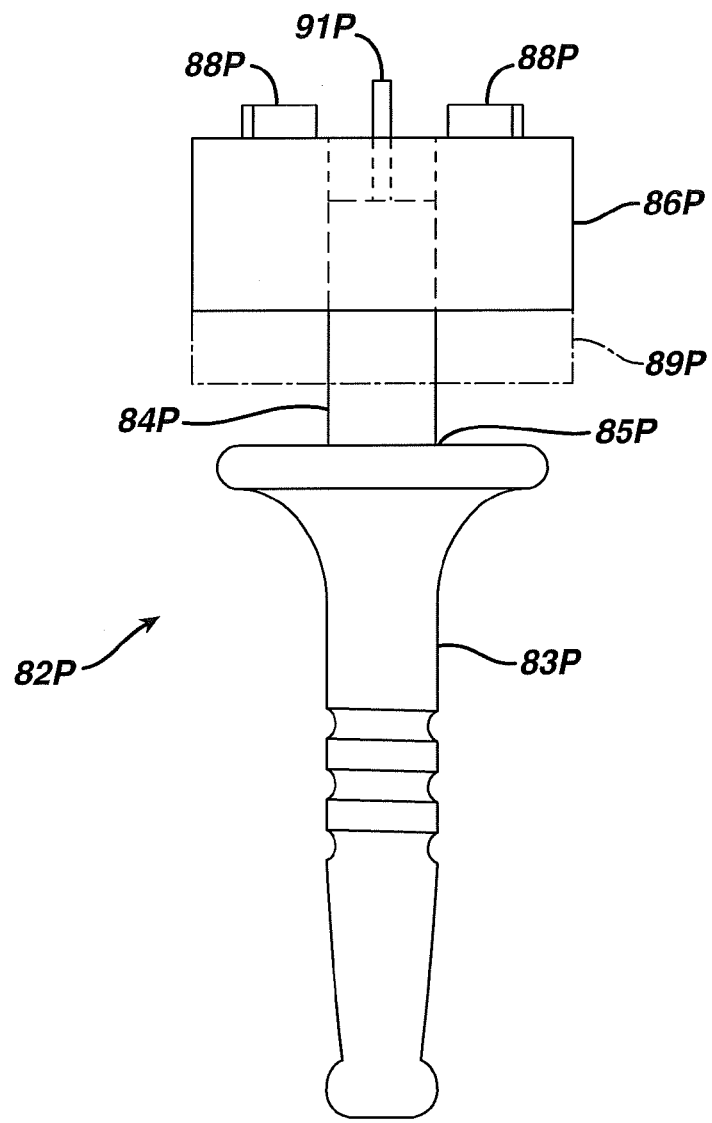
FIG. 1W is a top view of the cutter removal tool of FIG. 1V.
Figure 2:
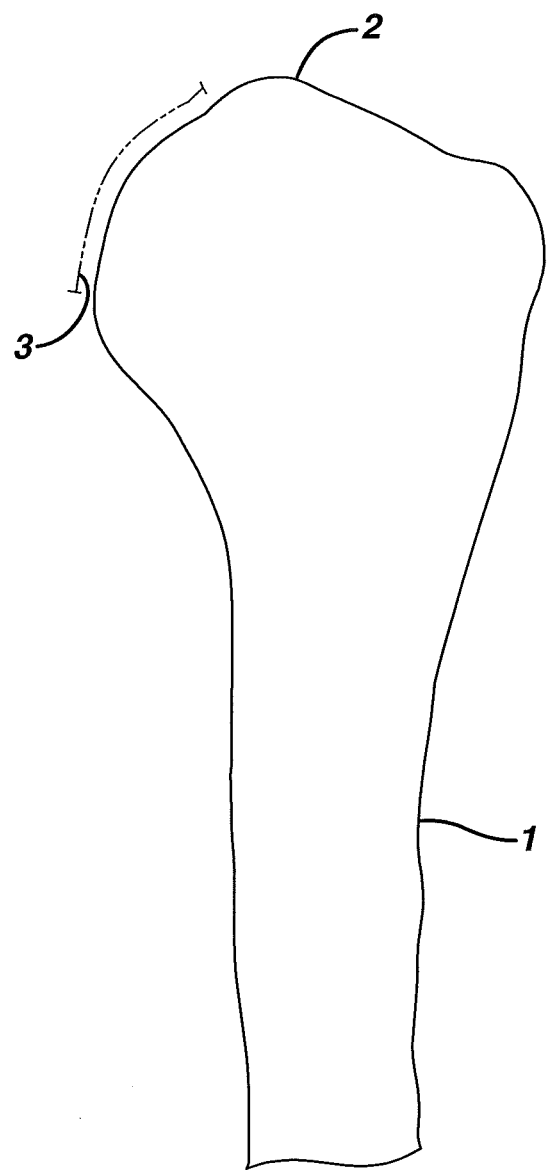
FIG. 2 is a plan of a healthy humerus.
Figure 3:
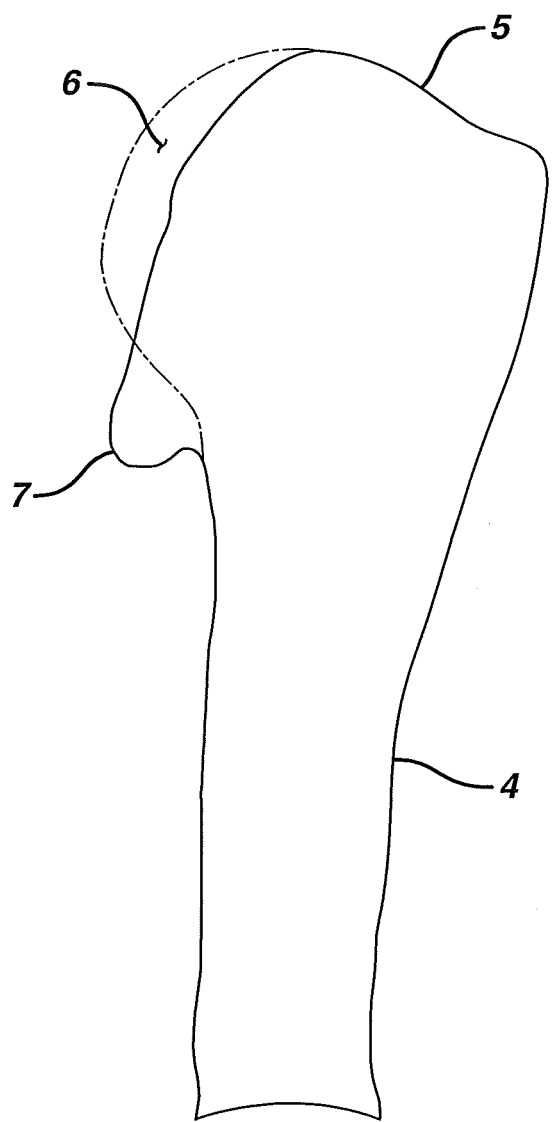
FIG. 3 is a plan of a diseased humerus.
Figure 4:
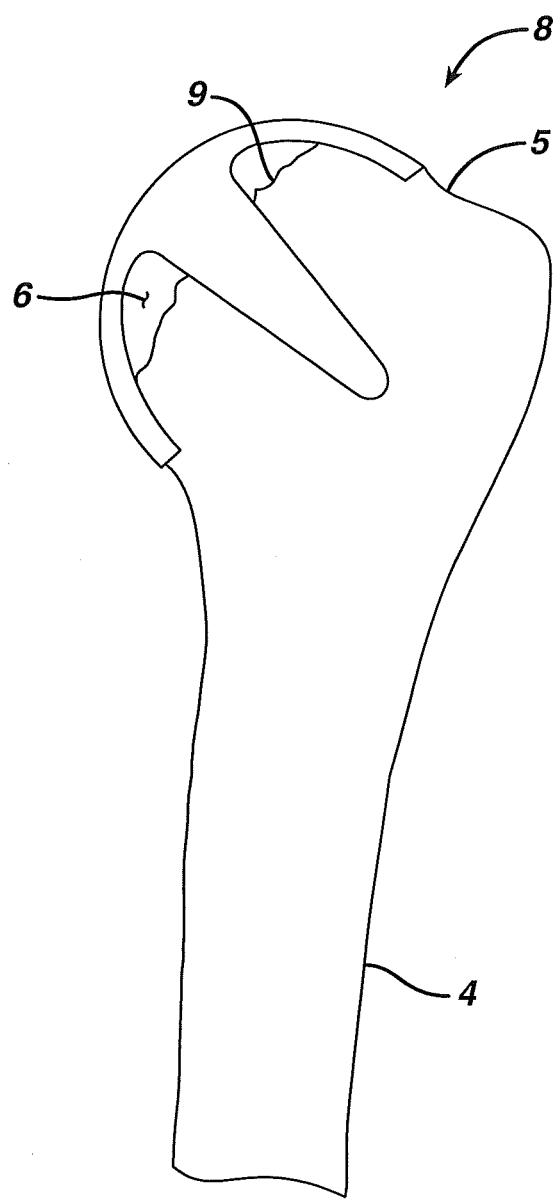
FIG. 4 is a plan view partially in cross section of a prior art humeral prosthesis.

Referring now to FIGS. 1V and 1W, a cutting tool assembly wrench 82P is shown. The wrench 82P performs the same function as the wrench 82 of FIG. 16, namely it secures the tool 10P to the driver 71P. The wrench 82P includes a cylindrical body 83P and a cylindrical shaft 84P extending from a first end 85P of the body 83P.

The wrench 82P further includes an adapter block 86P slidably fitted to the shaft 84P and the block 86P may move to position 89P (shown in phantom). A guide pin 91P is fixedly secured to shaft 84P and is used to align the wrench 82P to the tool 10P. Drive tangs 88P located on the block 86P engage with slots 87P (see FIG. Q) on the circular periphery 26P of the first portion 11P of tool 10P. The wrench 82P is rotated with respect to the tool 10P and a removal feature in the form of a bayonet mounting 38P on the shaft 37P of the tool 10P engages with the driver 71P.

Figure 5:
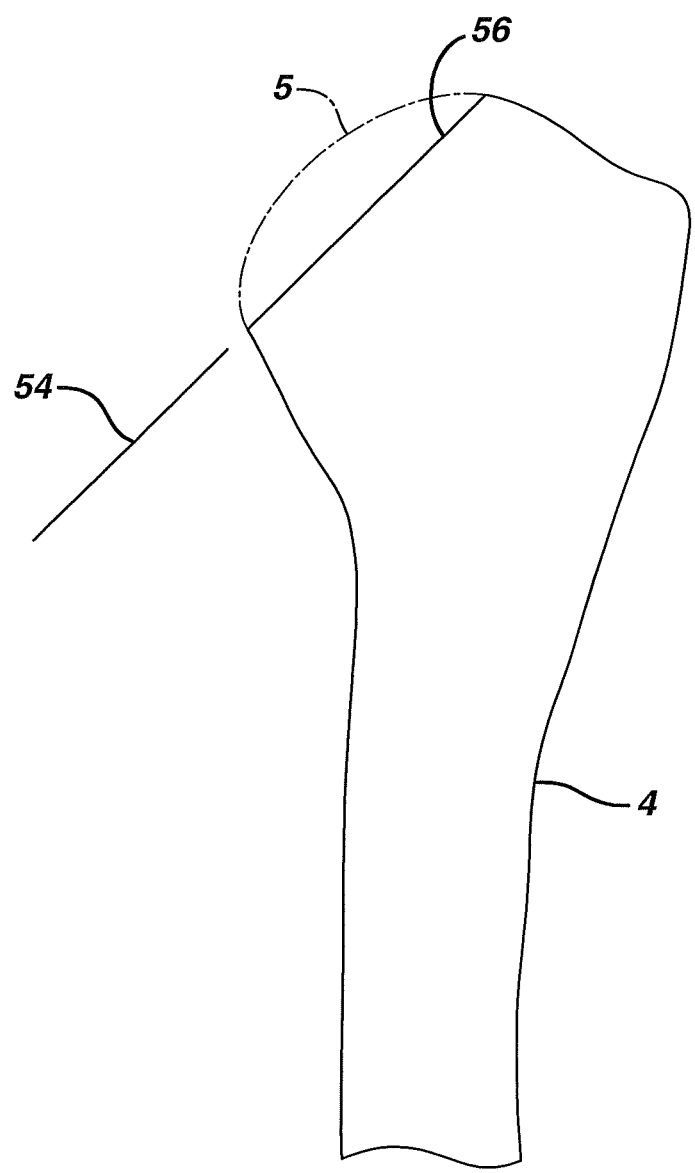
FIG. 5 is a plan view of a resected humerus showing the resected portion in phantom.
Figure 6:
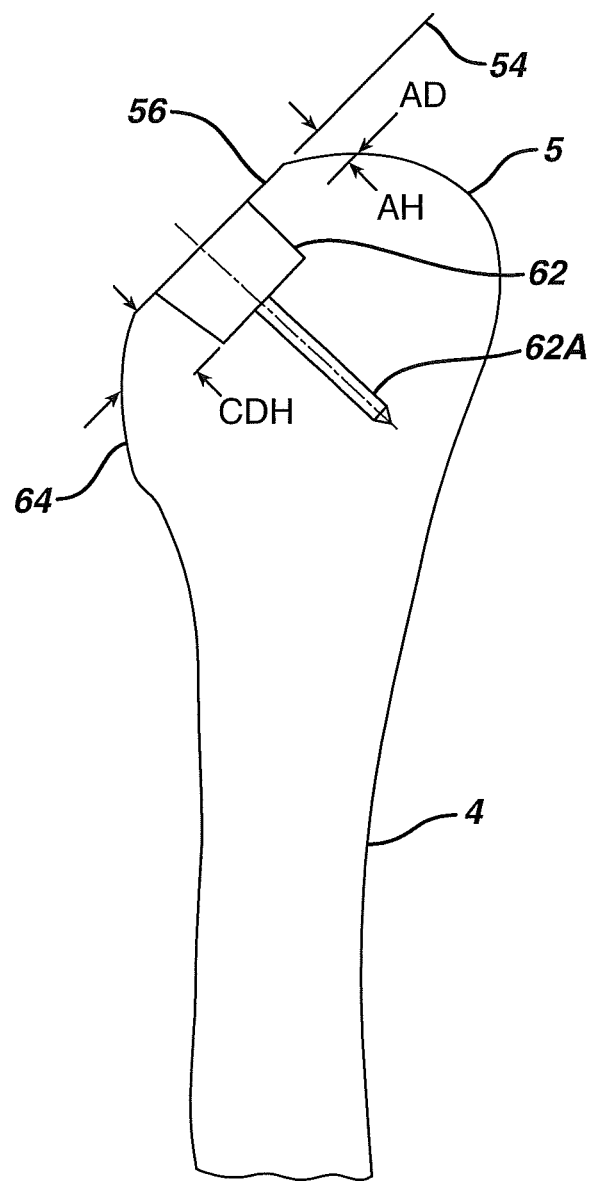
FIG. 6 is a plan view partially in cross section of a resected humerus with a cavity prepared with the reamer of the present disclosure.
Figure 7:
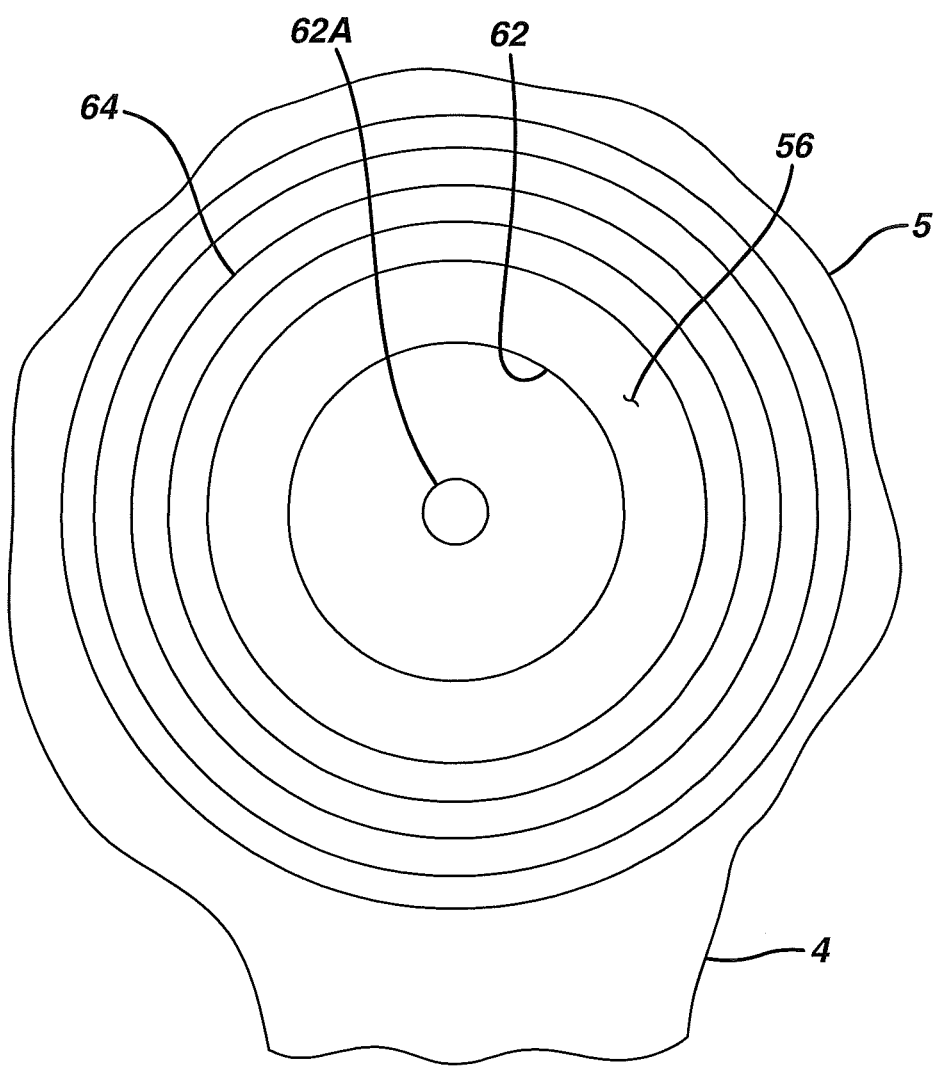
FIG. 7 is an auxiliary view of resected humerus with the cavity of FIG. 6 prepared with the reamer of the present disclosure.

Referring now to FIGS. 5, 6 and 7, a long bone in the form of a humerus 4 is shown in varying stages of preparation for receiving a prosthesis utilizing the gauge of the present invention as well as the surgical method of the present invention. Referring to FIG. 5, the humerus 4 is shown with a portion of the flattened head 5 resected. The head 5 is resected along resection line 54 providing a resected surface 56. The surface 56 may be resected by any suitable method, for example, a reamer, a mill end cutter, a saw, or an osteotome. The location of the resection line 54 may be determined by utilizing the gauge 410 of FIG. 17. The indicia 434 on the gauge 410 of FIG. 17 may be utilized to determine the position of the resection line 54 and the proper depth of the surface 56.

Referring now to FIGS. 6 and 7, the long bone in the form of humerus 4 is shown with the head 5 being prepared for a prosthesis used in conjunction with the instrument and surgical procedure of the present invention. Any suitable tool may be utilized to form the mounting hole or counter bore 62. For example, the mounting hole or counter bore 62 may be machined into the humerus 4 by use of a reamer. The counter bore 62 may be positioned a depth CDH from the resection line 54. The dimension CDH may be established utilizing the gauge 10 of FIG. 1. The gauge 410 of FIG. 17 may establish the proper prosthesis for a given bone contour and the dimension CDH may correspond to that recommended for that particular prosthesis.

The preparation of the head 5 of the humerus 4 may further include an arcuate support surface 64 formed adjacent the head 5. The arcuate surface 64 preferably conforms to that of the prosthesis and is generally arcuate and may be generally hemispherical. The arcuate surface 64 may be machined into the humerus 4 in any suitable fashion and may be machined by the reamer of the present invention. For example, the arcuate surface 64 may be applied by a grater-type reamer.

The position of the arcuate surface 64 may be determined by, for example, a depth AH at a diameter AD. The dimensions AD and AH may be determined with the assistance of the gauge 410 of FIG. 17. For example, the gauge 10 may be utilized to determine the proper prosthesis and the dimensions AH and AD may be determined upon that particular prosthesis.

Figure 17:
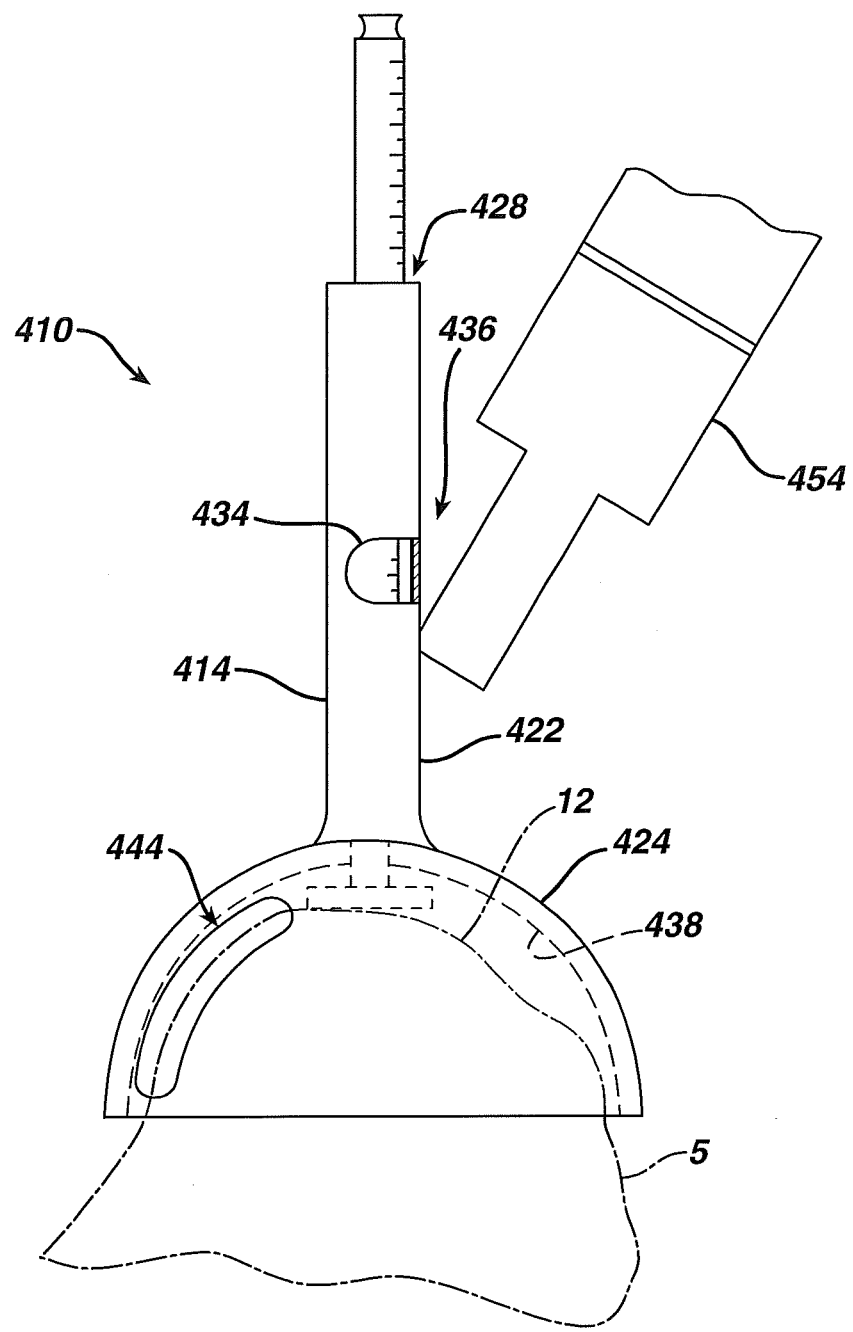
FIG. 17 is a plan view partially in cross section of a gauge with an offset handle for determining the appropriate spacer of a surface replacement prosthesis for use on a diseased humerus prepared with the reamer of the present disclosure.

The gauge 410 of FIG. 17, may be used to select the proper amount of resection to the humeral head and, correspondingly, the proper prosthesis to be used for that particular resection. It should be appreciated that due to the variations in the size of the patient and his or her respective humerus, a wide variety of prostheses may be required to accommodate the variations in a patient's humerus. Not only may the selection of a proper prosthesis be governed by the proper radius of the articulating surface, variations in the progress of the osteoarthritis may result in the flattening of the head of the humerus being in various stages of progression.

Due to the changes in the progression of the disease and the resulting shape of the humeral head, the resection plane may vary from being somewhat shallow to being much deeper into the humerus. Therefore, even for a given size of the articulating surface of the prepared natural humerus, the position of the resection, including the planar part of the resection of the humerus, may vary.

These various needs may be accomplished by providing a wide variety of sizes and configurations of the prosthesis. The availability of a wide variety of sizes and configurations of prostheses may be quite costly both in manufacturing lot sizes as well as in inventory. The applicants have discovered that the prosthesis may be made with more than one component.

Figure 8:
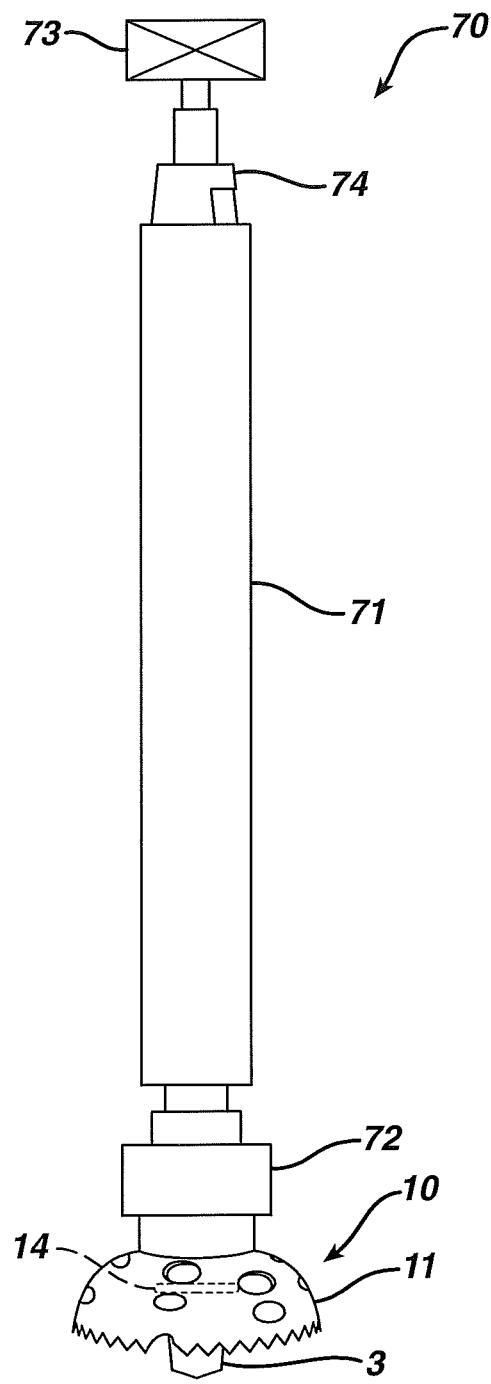
FIG. 8 is a plan view of a reamer assembly according to another embodiment of the present disclosure including a reamer and a reamer driver.

Referring now to FIG. 8, and according to another embodiment of the present invention, a cutting tool assembly 70 is shown. The cutting tool assembly 70 is utilized to perform arthroplasty, for example, a conservative or bone sparing arthroplasty to the head of a long bone. The cutting tool assembly 70 includes an instrument or cutting tool in the form of reamer 10. The reamer 10 includes first portion 11 adapted to prepare a convex surface, third portion 14 adapted to prepare a planar surface, and second portion 13 adapted to prepare an elongated cavity.

The cutting tool assembly 70 further includes a driver or tool holder 71. The driver 71 is releasably securable to the reamer 10. For example, the driver 71 includes a tool-releasing adapter 72, which is used to release the reamer 10 from the driver 71. Any standard available tool releasing adapter 72 may be utilized. As shown in FIG. 8, the driver 71 is adapted to be attachable to a power tool 73 to rotate the reamer 10. The power tool 73 may, for example, be a magnetic rotational tool, an electric rotational tool, or a hydraulic rotational tool, all commercially available. A driver adapter 74 may be utilized to attach the driver 71 to the power tool 73.

Figure 11:
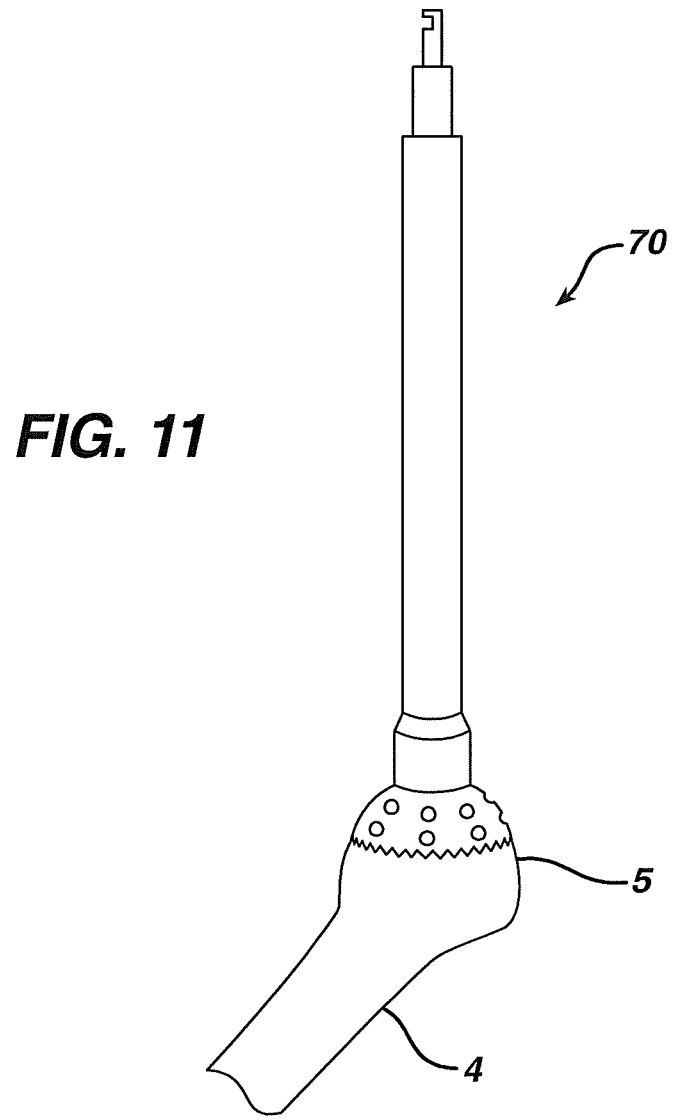
FIG. 11 is a perspective view of the reamer of FIG. 9 show in position on a humerus.

Referring to FIG. 11, the cutting tool assembly 70 is shown in position against humeral head 5 of humerus 4.

Figure 9:
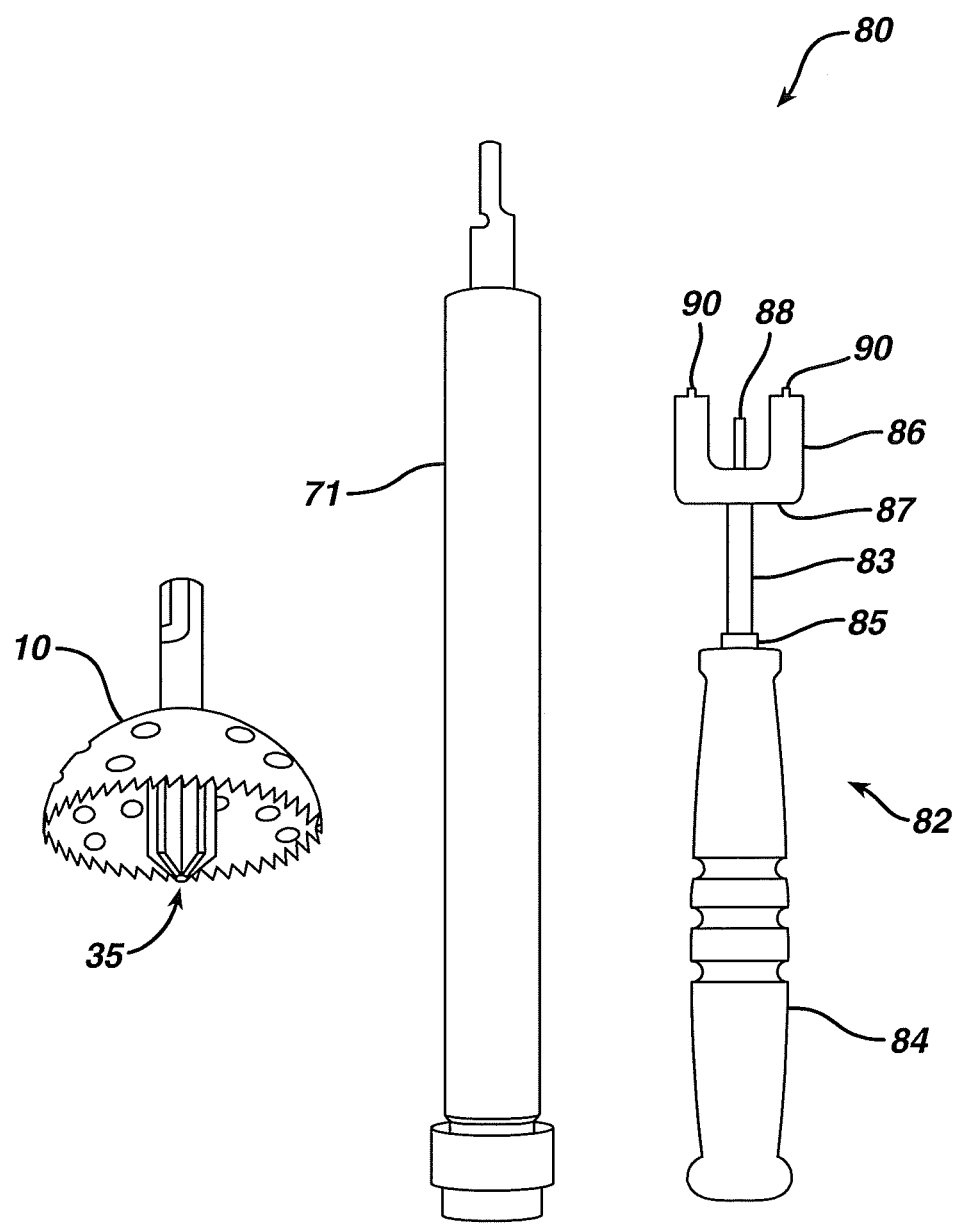
FIG. 9 is a perspective view of the reamer with a plan view of the reamer driver of FIG. 8 shown disassembled as well as a plan view of an assembly tool used to install the cutting reamer onto the reamer driver.
Figure 10:
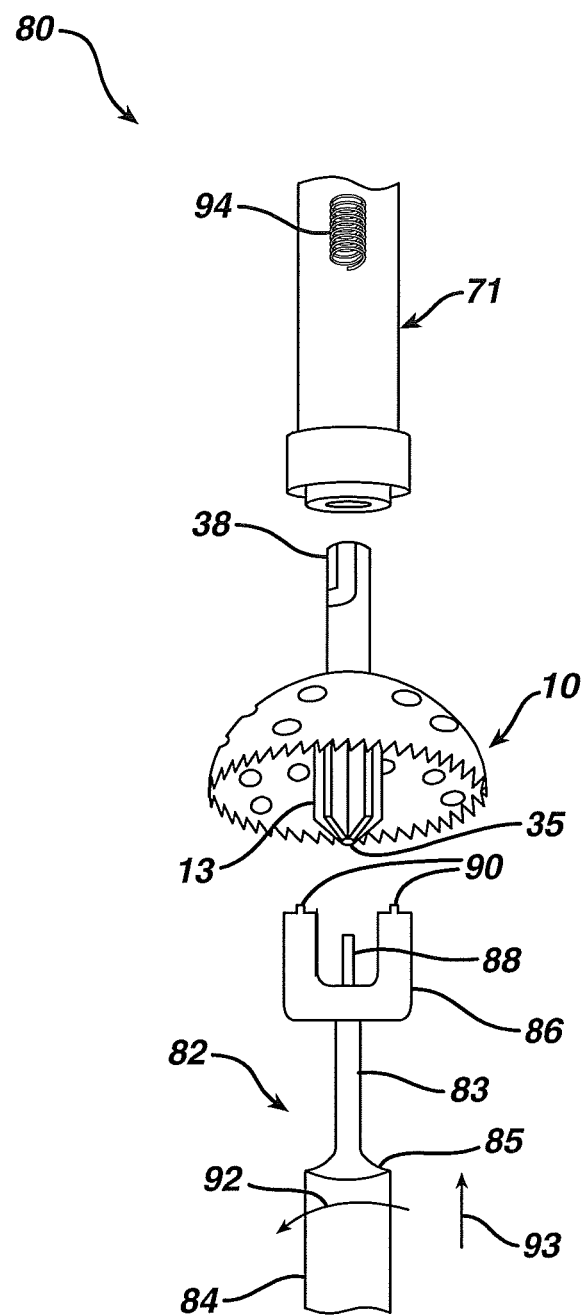
FIG. 10 is an exploded perspective view of the reamer of FIG. 1 and the reamer driver of FIG. 8 shown with an assembly tool used to attached the reamer to the reamer driver.

Referring now to FIGS. 9 and 10, the tool assembly kit 80 is shown. Referring to FIG. 9, the cutting tool assembly kit 80 includes the reamer or cutting tool 10 and the driver 71. The kit 80 further includes a cutting tool assembly wrench 82.

Figure 16:
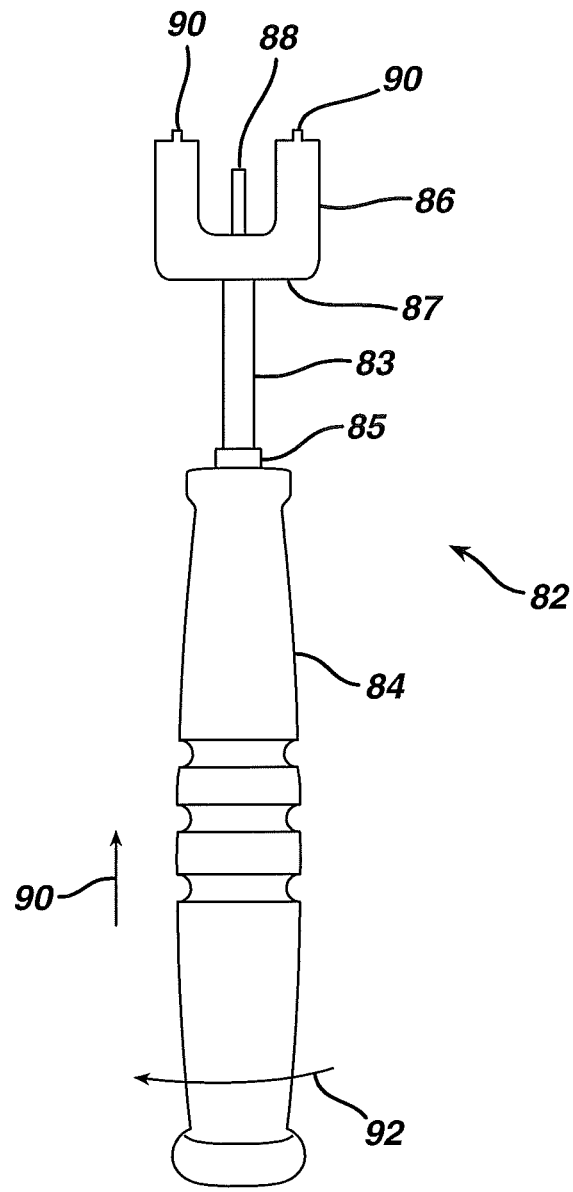
FIG. 16 is a plan view of the assembly tool of FIG. 10.

Referring now to FIGS. 10 and 16, the cutting tool assembly wrench 82 includes a cylindrical body 83 and a first handle 84 extending from a first end 85 of the body 83. The wrench 82 further includes a fork 86 extending from a second end 87 of the body 83.

The fork 86 includes a drive pin 88 for cooperation with the hole 35 of the second portion 13 of reamer 10 to guide the assembly wrench 82 into the reamer 10. The fork 86 further includes a pair of spaced-apart drive or engagement pins 90 which mate with openings (not shown) on the cutting tool or reamer 10.

By rotating the handle 84 of the wrench 82 in the direction of arrow 92 while pushing upward in a direction 93 and compressing spring 94 of the driver 71, the cutting tool pin may be released.

Figure 12:
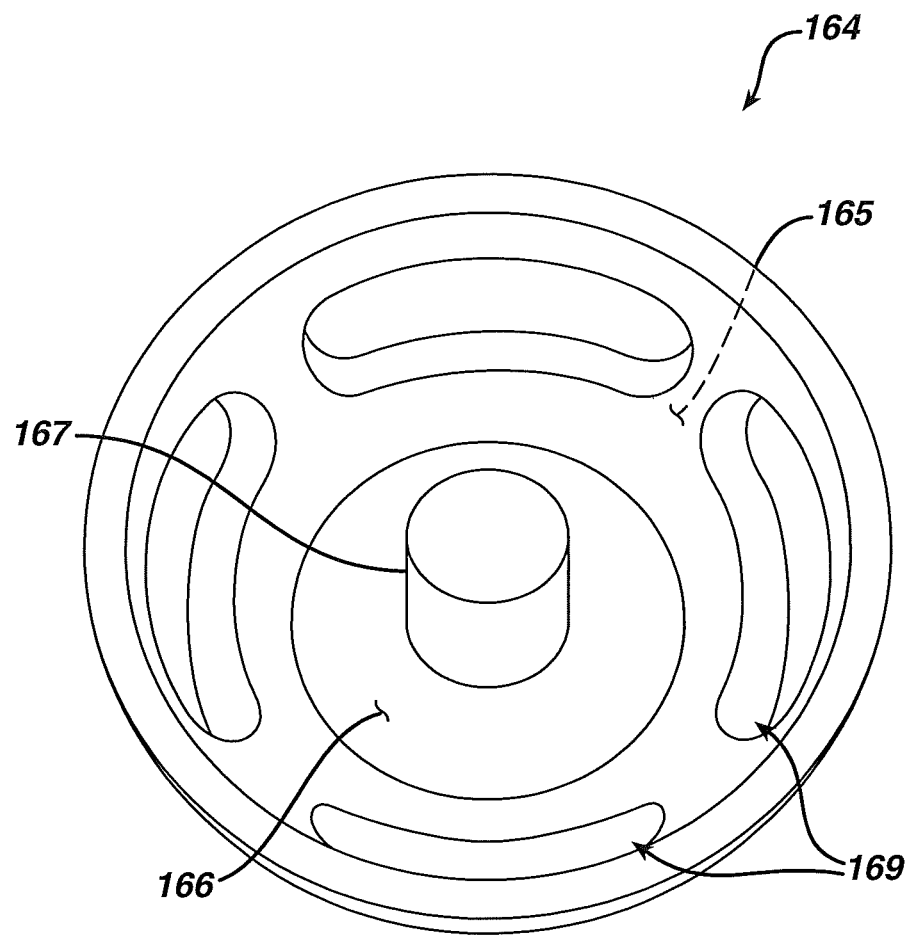
FIG. 12 is a perspective view of a trial for use on a humeral cavity prepared by the reamer of the present disclosure.

Referring now to FIG. 12 a trial 164 for use with the prosthesis of the present invention is shown. The trial 164 is utilized during shoulder arthroplasty to verify the proper selection of the prosthetic member by implanting the trial 164 into the humeral head and performing trial reductions on the arm to verify the selection of the particularly sized trial and corresponding prosthesis. The trial 164 is removed and replaced with the corresponding prosthesis. The trial 164 may be reused after sterilization. The trial is made of any suitable durable material and may, for example, be made of a durable plastic that may be sterilized by standard methods such as used in an autoclave.

The trial 164 mimics the size and shape of the prosthesis. The trial 164 therefore includes an articulating surface 165 and an opposed support surface 166. The trial 164 further includes a stem 167 extending outwarding from the support surface 166. As shown in FIG. 12, the trial 164 may also include a plurality of spaced apart openings 169 to assist in the removal of the trial 164.

Figure 13:
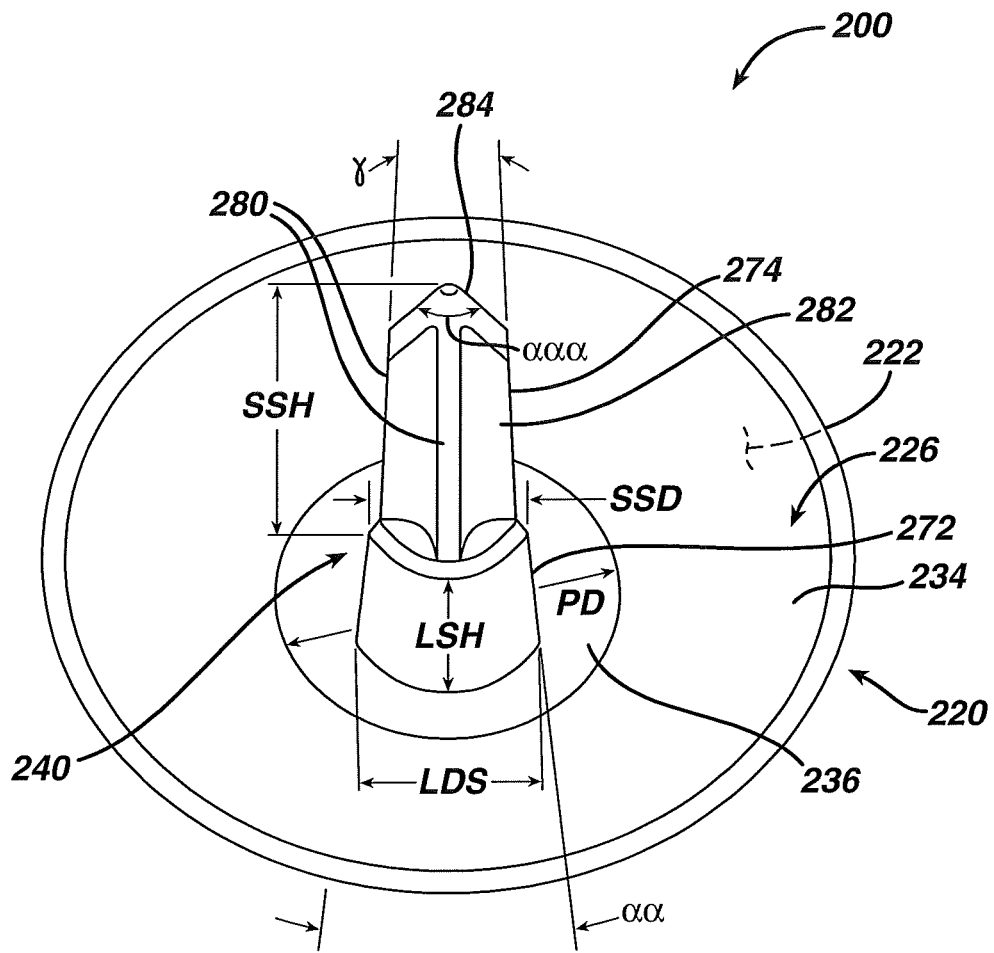
FIG. 13 is a perspective view of an implant for use on a humeral cavity prepared by the reamer of the present disclosure.
Figure 14:
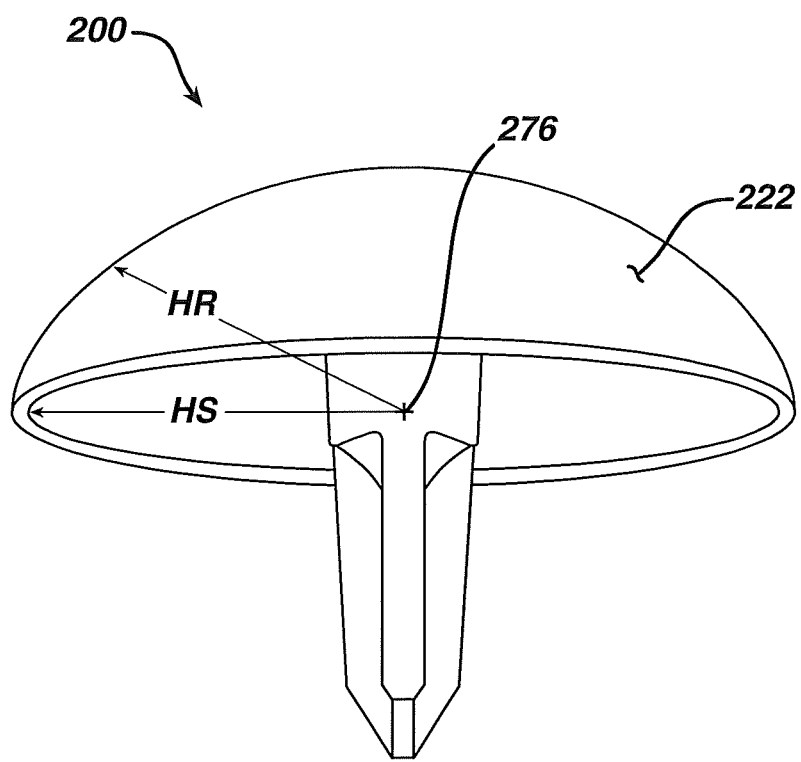
FIG. 14 is another perspective view of the implant of FIG. 13 for use on a humeral cavity prepared by the reamer of the present disclosure.

Referring now to FIGS. 13 and 14, an integral or one-piece humeral implant 200 is shown for use with the instrument of the present invention. The implant 200 may be made of any suitable durable material and may, for example, be made of a metal that is compatible with the human body. For example, the implant 200 may be made of a cobalt chromium alloy, a titanium alloy, or a stainless steel alloy.

The humeral implant 200 may include a body 220 having a arcuate articulating surface 222 and an opposed support surface 226. The support surface 226 may include an arcuate support surface 234 and a planar support surface 236. The humeral implant 200 may further include a stem 240 extending from the support surface 226 of the body 220. The stem 240 may be generally cylindrical and may, for example, be tapered.

For example and as shown in FIG. 13, the stem 240 may include a locating stem portion 272 extending from the support surface 226 and a securing stem portion 274 extending from the location stem portion 272.

The arcuate articulating surface 222 and the arcuate support surface 234 may both be hemispherical. For example, the articulating surface 222 may be defined by a radius HR extending from origin 276. Similarly, the arcuate support surface 234 may be defined by radius HS extending from the origin 276. The planar portion 236 of the support surface 226 may be generally disc-shaped and may be defined by diameter PD.

The locating stem portion 272 may be generally conifrustrical and may be defined by diameter LDS and length LSH, as well as, by included angle .alpha..alpha.. Similarly, the securing stem portion 274 may be generally conifrustrical and be defined by diameter SSD and length SSH as well as by angle .gamma. The securing stem portion 274 may include a plurality of spaced-apart flutes 280 separated by recesses 282. A tip 284 may extend outwardly from the securing stem portion 274 at an angle .alpha..alpha..alpha.

Figure 15:
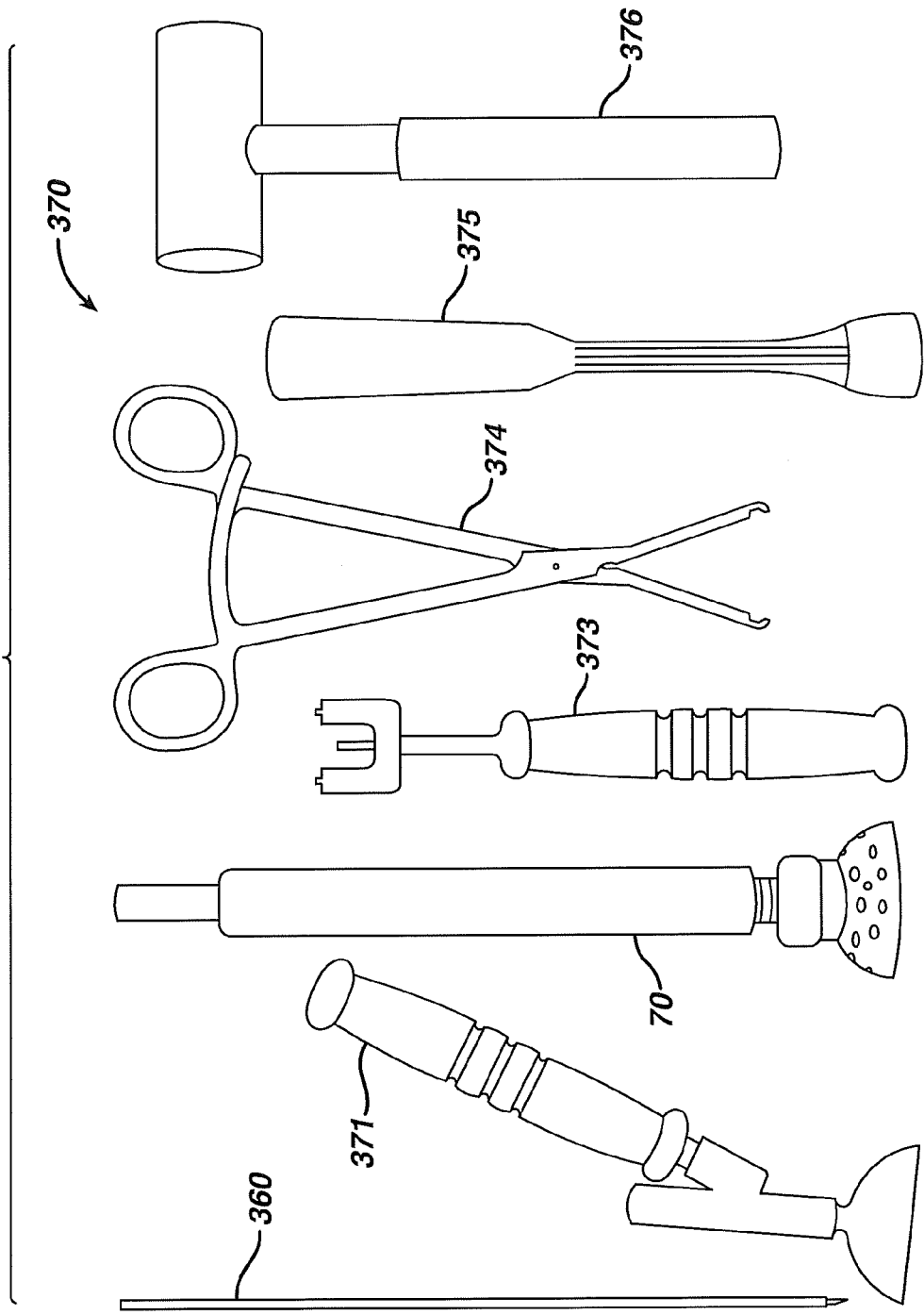
FIG. 15 is a plan view of set of surgical instruments that may be used in performing shoulder arthroplasty according to a further embodiment of the present disclosure.

Referring now to FIG. 15, a kit 370 for use when performing an arthroplasty to implant the prosthesis of the present invention. The kit 370 includes the guide pin 360, a guide pin alignment tool 371 for assisting in aligning the guide pin and positioning it into the humerus. The instrument kit 370 also includes the cutting tool assembly 372 for preparing the humeral head. The instrument kit 370 further includes the cutting tool assembly wrench 373 for assembling and disassembling the cutting tool from the cutting tool assembly 372. The instrument kit 370 also includes forceps 374 for securely gripping items. The instrument kit 370 also includes a humeral head impactor 375, which is used with a surgical mallet 376 to drive the implant into its final seat.

Referring now to FIG. 17, a gauge 410 for use in measuring the flattening of the natural humerus is shown. The gauge 410 is used to assist in selecting the proper sized implant. The gauge 410 is designed to assist in the ease of viewing the position of the gauge with respect to the bone contour 12.

As shown in FIG. 17, the gauge 410 includes a body 414 having a cylindrical portion 422. The body 414 further includes a hollow hemispherical portion 424, which has an inner periphery 438, which minimizes the locating surface of the implant. The cylindrical portion 422 includes a longitudinal cylindrical opening 428 as well as an indicia opening 436 for viewing indicia 434. The hemispherical portion 424 includes a viewing window 444 to view the head 5 in assisting the proper positioning of the gauge 410.

As shown in FIG. 17, the gauge 410 includes a separate handle 454 separate from the cylindrical body 422. The handle 454 is utilized for holding the gauge 410 in position with respect to the head 5. It can be seen that the handle 454 is preferably opposed to the viewing window 444 so that the head 5 may be clearly viewed through the viewing window 444 while the gauge 410 is being held by the handle 454.

Figure 18:
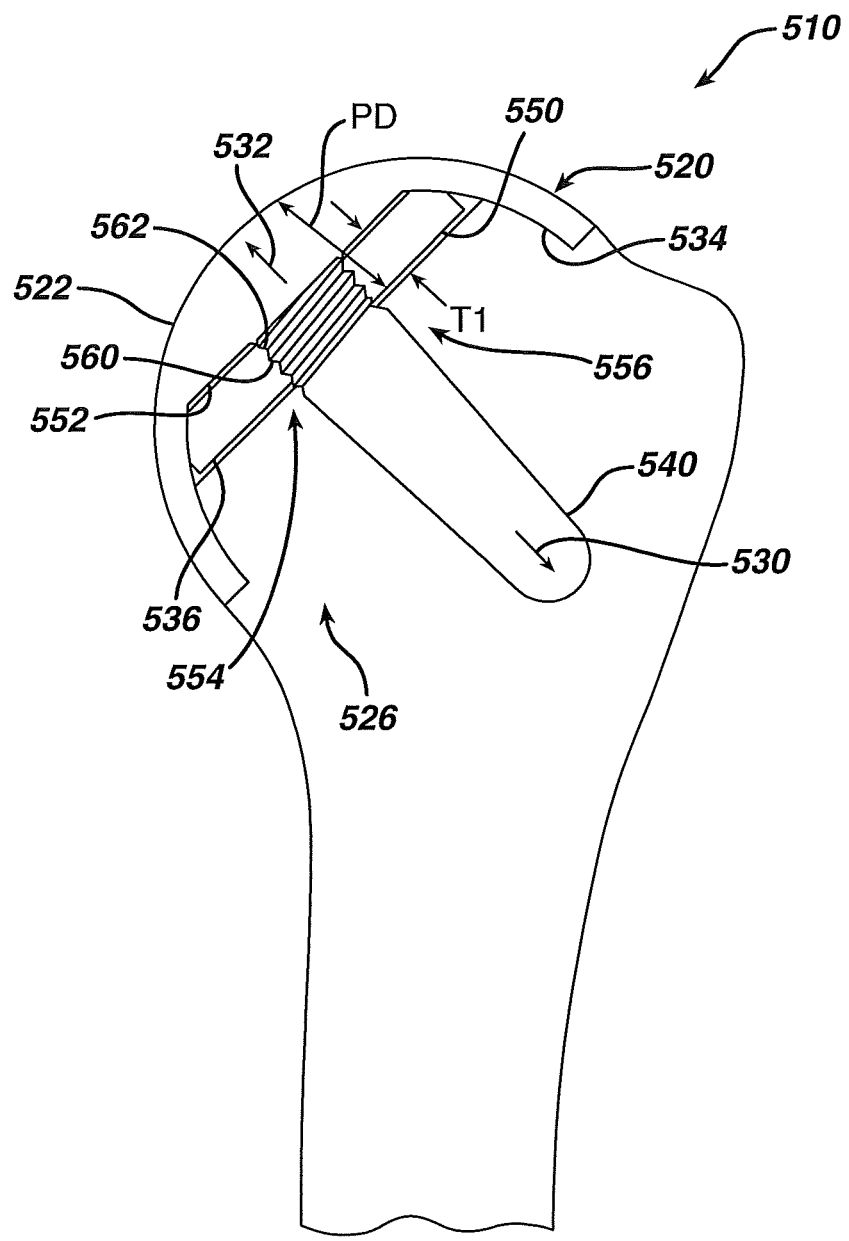
FIG. 18 is a plan view partially in cross section of a surface replacement prosthesis with a screwed-on spacer for use on the prepared humerus prepared by the reamer of the present disclosure.

Referring now to FIG. 18, an example of a multi-piece prosthesis is shown as prosthesis 510. Prosthesis 510 of FIG. 18 is similar to the prosthesis 200 of FIG. 13 except that the prosthesis 510 is made of two components rather than the solitary component of the prosthesis 200 of FIG. 13.

As shown in FIG. 18, the prosthesis 510 includes in addition to a body 520, a spacer 550. The spacer 550 provides for a variety of locations of the planar portion 536 of support surface 526. Thus, by utilizing the prosthesis 510, a common body 520 may be used with a variety of spacers 550 having different thicknesses T1. Thus, for any prosthesis 510 a plurality of planar dimensions PD may be provided by merely changing the spacer 550 to either a thinner or a thicker spacer.

As shown in FIG. 18, the prosthesis 510 includes the body 520. The body 520 includes an articulating surface 522 extending in a second direction 532 as well as a stem 540 extending in a first direction 530 opposed to the second direction 532.

As shown in FIG. 18, the body 520 includes a body planar surface 552 to which the spacer 550 is placed. The spacer 550 defines the planar portion 536 of the support surface 526 and works in conjunction with arcuate surface 534 of the body 520 to support the prosthesis 510 against the humerus wall.

As shown in FIG. 18, the spacer 550 preferably has a pair of spaced apart parallel faces defined with the thickness T1. The spacer 550 has a central opening 554 to permit the spacer 550 to be positioned in place against the body planar surface with the stem 540 passing through the opening 554.

Preferably, and as shown in FIG. 18, the spacer 550 is secured to the body 520 by, for example, a connector 556. The connector 556 may, as shown in FIG. 5, be in the form of a threadable connection. For example, the connector 556 may include external threads 560 located on the distal portion of the stem 540. The external threads 560 on the stem 540 cooperate with matching internal threads 562 on the spacer 550. A feature (not shown) in the form of, for example, a recess on the planar portion 536 of the spacer 550 may be utilized to secure the spacer 550 against the body 520. The body 520 and the spacer 550 may be made of a similar material to that of the prosthesis 200. Thus, for example, the body 520 and the spacer 550 may be made of a cobalt chromium alloy, a titanium alloy or a stainless steel alloy.

Figure 19:
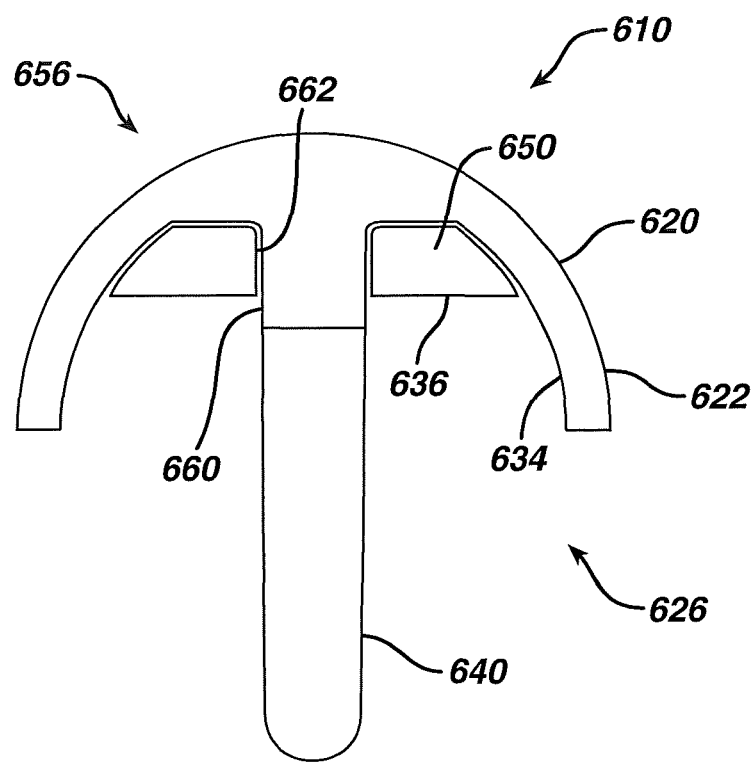
FIG. 19 is a plan view partially in cross section of another embodiment of a surface replacement prosthesis with a tapered fit spacer for use on the prepared humerus prepared by the reamer of the present disclosure.

Referring now to FIG. 19, another embodiment of the present invention as prosthesis 610. Prosthesis 610 includes a body 620 similar to the body 520 of the prosthesis 510 of FIG. 18 in that the body 620 includes stem 640 similar to stem 540 of FIG. 18. The prosthesis 610 further includes a spacer 650 similar to the spacer 550 of the prosthesis 510 of FIG. 18.

The spacer 650 is secured to the body 620 by means of a connector 656. The connector 656 is different that the connector 556 of the prosthesis 510 in that the connector 656 is in the form of a taper fit. The spacer 650 includes a tapered opening 662 which engages with tapered stem portion 660 of the stem 640 of the prosthesis 610. The body 620 includes an articulating surface 622 and an opposed arcuate support surface 634. The spacer 650 includes a planar support surface 636 which together with the arcuate support surface 634, form the support surface 626 for supporting the prosthesis 610 within the humerus 12.

Figure 20:
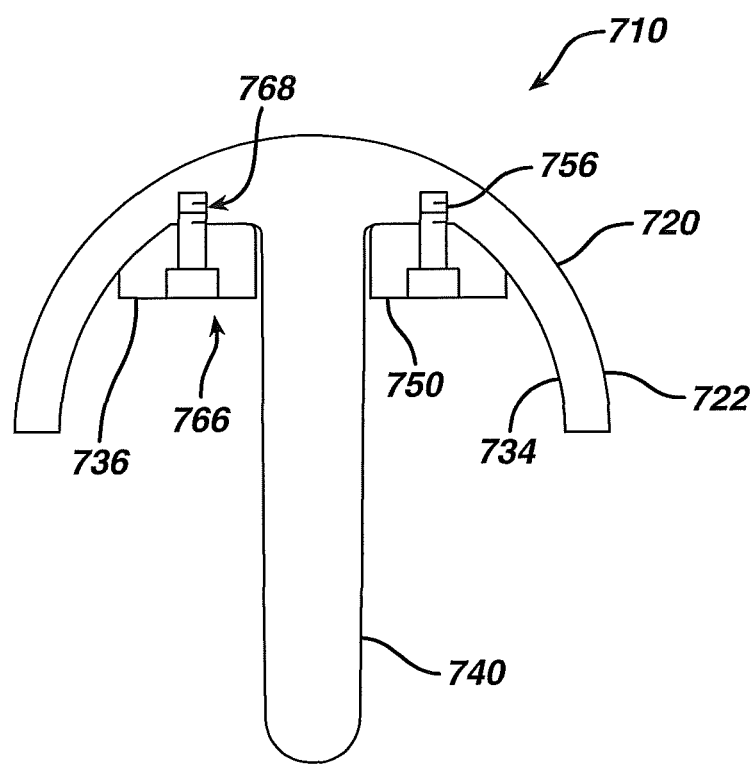
FIG. 20 is a plan view partially in cross section of another embodiment of a surface replacement prosthesis with a bolted-on spacer for use on the prepared humerus prepared by the reamer of the present disclosure.

Referring now to FIG. 20, another embodiment of the present invention is shown as prosthesis 710. The prosthesis 710 of FIG. 20 is similar to the prosthesis 610 of FIG. 19, and includes a body 720 similar to the body 620 of FIG. 19. The body 720 includes an articulating surface 722 and an opposed arcuate support surface 734. The body 720 in integral with a stem 740 similar to the stem 640 of FIG. 19. The prosthesis 710 further includes a spacer 750 similar to the spacer 650 of the prosthesis 610 of FIG. 19.

The spacer 750 is secured to the body 720 of the prosthesis 710 by means of a connector 756, which is different than the connector 656 of the prosthesis 610 of FIG. 19. The connector 756 is in the form of a plurality of socket head hex cap screws. The cap screws 756 are fitted into recessed openings 766 in the spacer 750. The cap screws 756 are secured to the body 720 by a plurality of threaded openings 768. The spacer 750 provides planar support surface 736.

Figure 21:
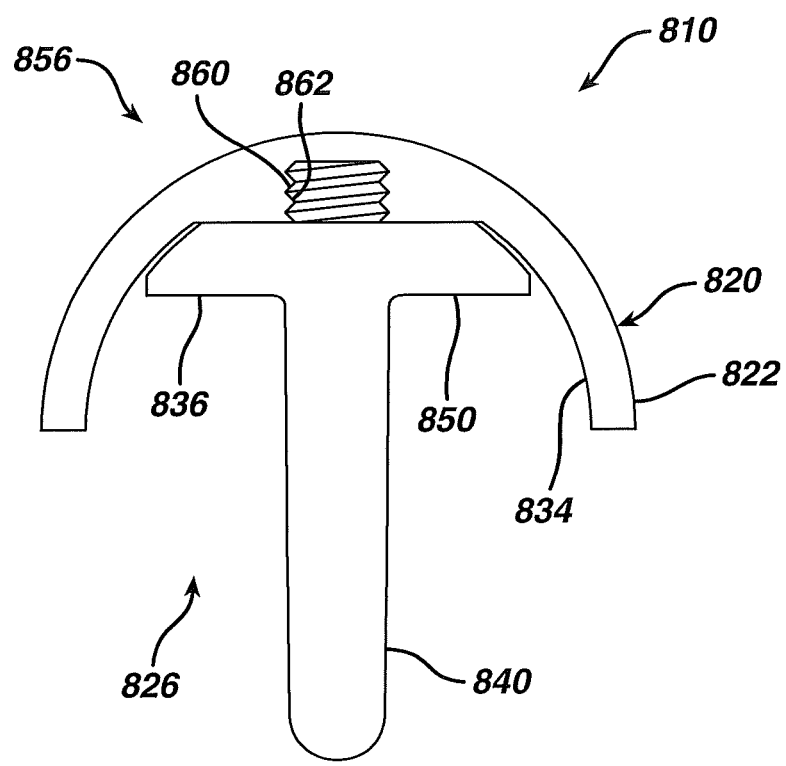
FIG. 21 is a plan view partially in cross section of another embodiment of a surface replacement prosthesis with a bolted-on spacer and stem for use on the prepared humerus prepared by the reamer of the present disclosure.

Referring now to FIG. 21, another embodiment of the present invention is shown as prosthesis 810. Prosthesis 810 is similar to the prosthesis 200, 510, 610 and 710 in that the prosthesis 810 includes a body 820, a spacer 850, and a stem 840. The prosthesis 810 is different than the prosthesis 200, 510, 610 and 710 in that the spacer 850 and the stem 840 are integral with each other. The body 820 of the prosthesis 810 thus does not include the stem 840 and is a separate part from the spacer 850 and the stem 840.

As shown in FIG. 9, the body 820 has a generally hollow hemispherical shape having a articulating surface 822 and an opposed arcuate support surface 834. The spacer 850 has a general disc shape with the stem 840 having a generally cylindrical shape and extending outwardly from the center portion of the spacer 850.

The spacer 850 is secured to the body 820 by means of a connector 856. The connector 856 as shown in FIG. 21 is in the form of a threaded stem extending from the spacer 850 in a direction opposed to the stem 840. The connector 856 includes external threads 860, which mate with internal threads 862 in the body 820. The spacer 850 forms planar support surface 836, which together with the arcuate support surface 834 forms support surface 826 for supporting the prosthesis 810 against the humerus 12.

Figure 22:
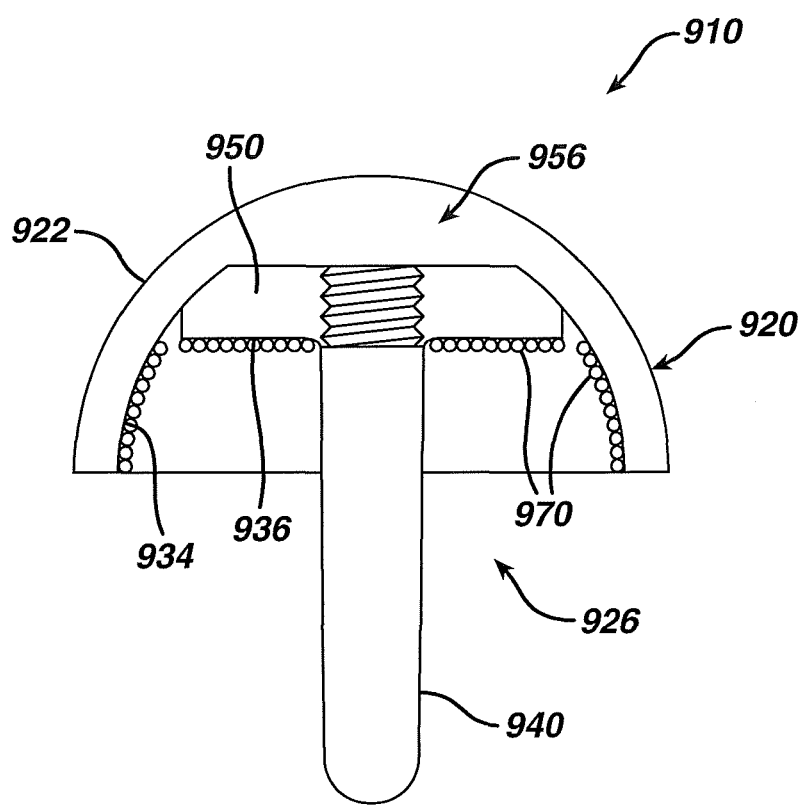
FIG. 22 is a plan view partially in cross section of another embodiment of a surface replacement prosthesis with a screwed-on spacer with a portion of the prosthesis having porous coating for use on the prepared humerus prepared by the reamer of the present disclosure.

Referring now to FIG. 22, another embodiment of the present invention is shown as prosthesis 910. Prosthesis 910 is similar to the prosthesis 810 of FIG. 21. Prosthesis 910 includes a body 920 similar to the body 820 of FIG. 21 and includes an articulating surface 922 and opposed arcuate support surface 934. The body 920 includes a stem 940 similar to the stem 840 of FIG. 21. The prosthesis 910 further includes a spacer 950 similar to the spacer 850 of FIG. 21. The spacer 950 includes a planar support surface 936, which together with the arcuate support surface 934 serves to form support surface 926 for supporting the prosthesis 910 against the humerus 12. The prosthesis 910 further includes a connector 956 similar to the connector 556 of the prosthesis 510 of FIG. 18.

Unlike the prosthesis 110, the prosthesis 910 includes a porous coating 970 located on the planar support surface 936 and the arcuate support surface 934. The porous coating 970 serves to provide additional surface for promoting bony ingrowth into the prosthesis 910 for improved fixation of the prosthesis 910 to the humerus 12. Any suitable commercially available porous coating may be suitable for the coating 970. For example, the coating may be in the form of POROCOAT®, a product of the assignee of the instant application. More information regarding the coating may be available by referring to U.S. Pat. No. 3,855,638 to Pilliar incorporated herein by reference in its entirety.

Figure 23:
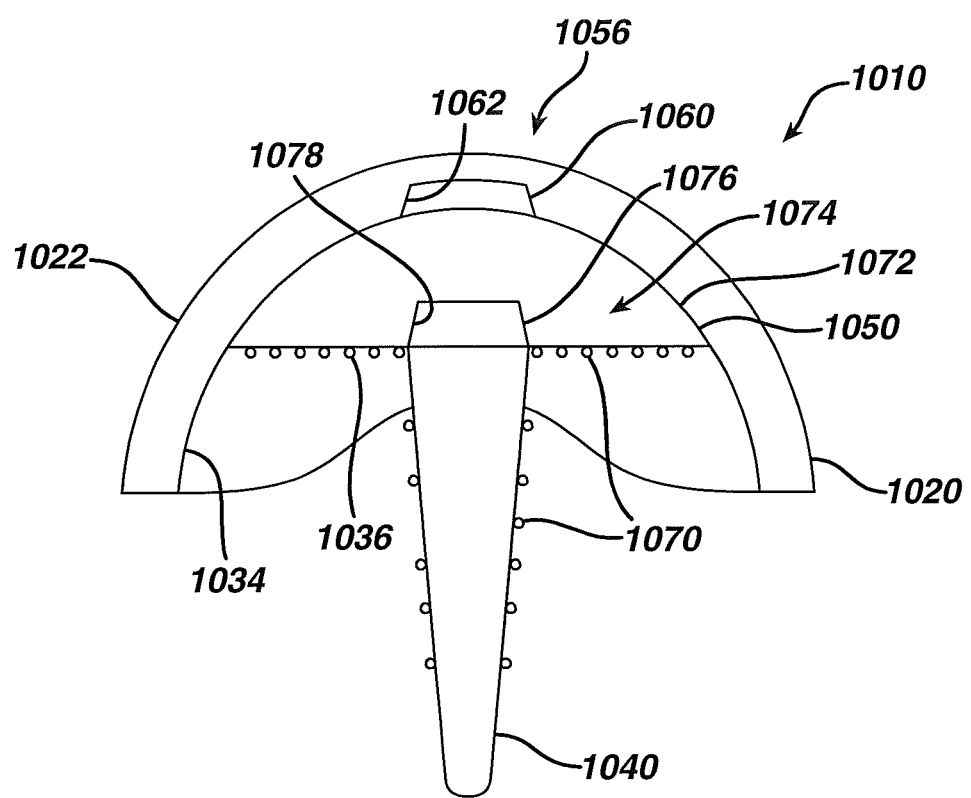
FIG. 23 is a plan view partially in cross section of another embodiment of a surface replacement prosthesis with a three piece cup, spacer and stem assembly with porous coating for use on the prepared humerus prepared by the reamer of the present disclosure.

Referring now to FIG. 23, another embodiment of the present invention is shown as prosthesis 1010. Prosthesis 1010 is a three-part prosthesis including a body 1020 similar to the body 920 of the prosthesis 910 of FIG. 22. The body 1020 includes a hemispherical outer articulating surface 1022 and a concave internal arcuate support surface 1034. The prosthesis 1010 further includes a plug 1050, which serves the purpose of the spacer 950 of the prosthesis 910 of FIG. 22. The plug 1050 includes a planar support surface 1036 and an opposed spherical outer surface 1072 which mates with the arcuate support surface 1034 of the body 1020. The plug 1050 may be secured to the body 1020 by any suitable method. For example, as shown in FIG. 23, a first connector 1056 in the form of a taper connection is shown.

The first connector 1056 includes an exterior taper 1060 extending from the plug 1050, which mates with an internal taper 1062 in the body 1020. The prosthesis 1010 further includes a generally cylindrical tapered stem 1040, which is secured to the plug 1050 by a second connector 1074.

The stem 1040 may be secured to the plug 1050 by, for example, a second connector 1074. The second connector 1074 may have any suitable configuration and may, as shown in FIG. 23, be in the form of an external taper 1076 located on the stem 1040, which cooperates with an internal taper 1078.

As shown in FIG. 23, the prosthesis 1010 may further include a coating 1070 in the form of, for example, a porous coating, for example, POROCOAT® to encourage ingrowth to assist in the securement of the prosthesis 1010 to the humerus 12. The coating 1070 may be secured to the stem 1040 as well as to the arcuate support surface 1034 as well as the planar support surface 1036.

Figure 24:
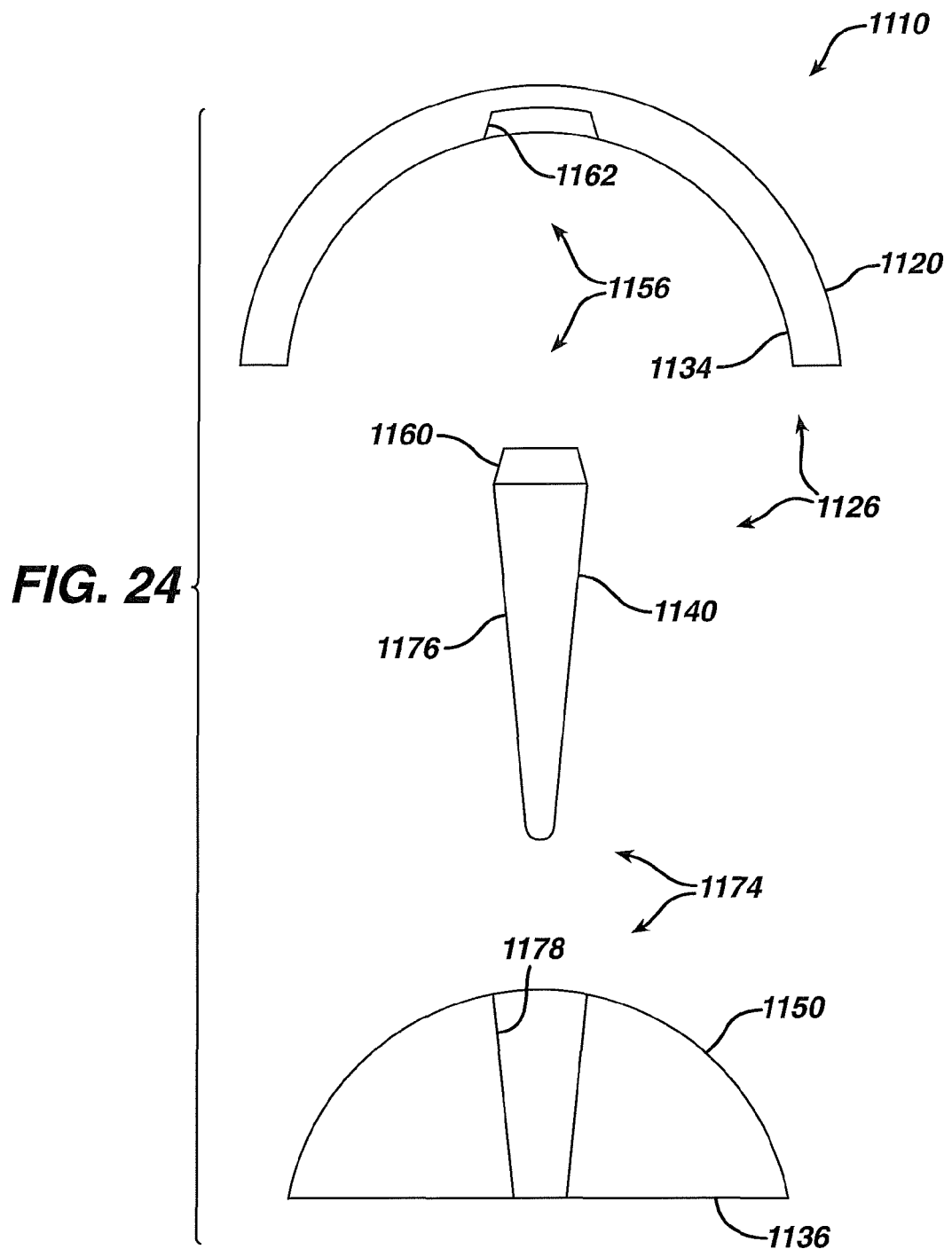
FIG. 24 is an exploded plan view partially in cross section of another embodiment of a surface replacement prosthesis with a three piece cup, plug and stem assembly for use on the prepared humerus prepared by the reamer of the present disclosure.

Referring now to FIG. 24, another embodiment of the present invention is shown as prosthesis 1110. Prosthesis 1110 is similar to prosthesis 1010 of FIG. 23 and includes three components, namely a body 1120 similar to body 1020 of the prosthesis 1010 of FIG. 23, a stem 1140 similar to the stem 1040 of the prosthesis 1010 of FIG. 23, and a plug 1150. The plug 1150 is similar to the plug 1050 of the prosthesis 1010 of FIG. 23 except that the plug 1150 and the stem 1140 are secured to the body 1120 in a different fashion from that of the prosthesis 1010. While the prosthesis 1110 similar to the prosthesis 1010, in that it has its components interconnected by means of tapered connections, the tapered connections of the prosthesis 1110 are different from those of the prosthesis 1010 of FIG. 23.

For example, the prosthesis 1110 includes a first connector 1156 in the form of a tapered connection. The tapered connection 1156 includes an external taper 1160 formed on the stem 1140, which connects with an internal taper 1162 formed on the body 1120.

The plug 1150 is secured to the stem 1140 by means of a second tapered connection 1174. The second tapered connection 1174 includes an external taper 1176 formed on the stem 1140 which connects with an internal taper 1178 formed on the plug 1150. The plug 1150 includes a support surface 1136 which, together with arcuate surface 1134 of the body 1120 form support surface 1126 of the prosthesis 1110 for securing the prosthesis 1110 to the humerus 12.

Figure 25:
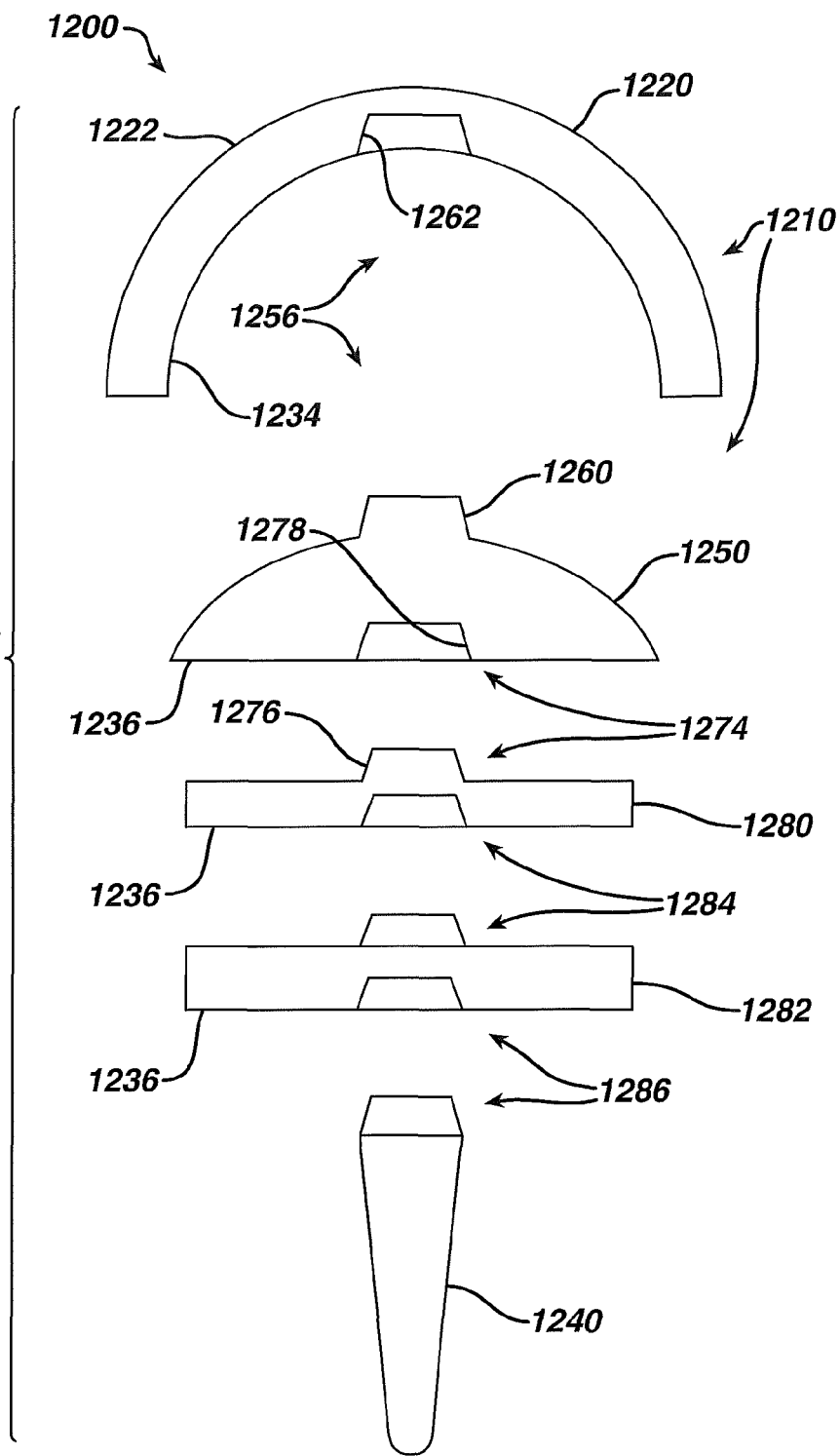
FIG. 25 is an exploded plan view partially in cross section of another embodiment of a surface replacement prosthesis kit with a three-piece construction including a cup, a set of two spacers and a stem for use on the prepared humerus prepared by the reamer of the present disclosure.

Referring now to FIG. 25, another embodiment of the present invention is shown as kit 1200. The kit 1200 includes a body 1220 similar to the body 1020 of the prosthesis 1010 of FIG. 23. The body 1220 includes an articulating surface 1222 and an opposed support surface 1234. The kit 1200 further includes a first spacer in the form of a plug 1250. The first spacer 1250 is similar to the first spacer or plug 1050 of the prosthesis 1010 of FIG. 23. The body 1220 and the first spacer 1250 combine to form prosthetic member 1210. The prosthetic member 1210 may further include an optional stem 1240 similar to the stem 1040 of FIG. 23.

The kit 1210 in addition to the first spacer 1250 includes a second spacer 1280. The second spacer 1280 may selectively be included or excluded from the prosthetic member 1210 such that planar support surface 1236 may be located for example on the first spacer 1250 or alternatively on the second spacer 1280. The kit 1200 may optionally further include a third spacer 1282 or additional spacers (not shown).

When the kit 1200 includes the body 1220, the first spacer 1250 and the second spacer 1280, the kit 1200 may be utilized by selectively picking the inclusion or non-inclusion of the second spacer 1280, thereby providing for a variation in the location of the support surface 1236.

The kit 1200 serves to permit the use of a prosthesis with a variety of locations for the support surface 1236. The ability to vary the location of the support surface is important when dealing with diseased humerus in which the flattened head may vary from patient to patient, and the corresponding required amount of resection may vary for a given geometry of the humerus.

The prosthetic of kit 1200 may be built by utilizing the body 1220 and the plug 1250 as well as a combination of one or the other of the second and third spacers 1280 or 1282, respectively, or by the use of both spacers 1280 and 1282. Similarly, the prosthetic member 1210 may be performed without the use of either the second spacer 1280 or the third spacer 1282.

Preferably and as shown in FIG. 25, the first spacer 1250 is secured to the body 1220 by use of a first tapered connection 1256. The first tapered connection 1256 as shown in FIG. 25, includes an external taper 1260 formed on the first spacer 1250, which mates with an internal taper 1262 formed on the body 1220.

The second spacer 1280 may be secured to the plug 1250 by the use of a second tapered connection 1274. The second tapered connection 1274 may include an external taper 1276 formed on the second spacer 1280 which mates with an internal taper 1278 formed in the first spacer 1250. Similarly, the second spacer 1280 may be connected to the third spacer 1282 by means of a third tapered connection 1284. Similarly, the third spacer 1282 may be connected to the stem 1240 by means of a fourth tapered connection 1286.

Preferably and as shown in FIG. 25, the second tapered connection 1274, the third tapered connection 1284 and the fourth tapered connection 1286 are identical to each other so that the stem 1240 may be connected to any of the first spacer 1250, second spacer 1280 or third spacer 1282.

Figure 26:
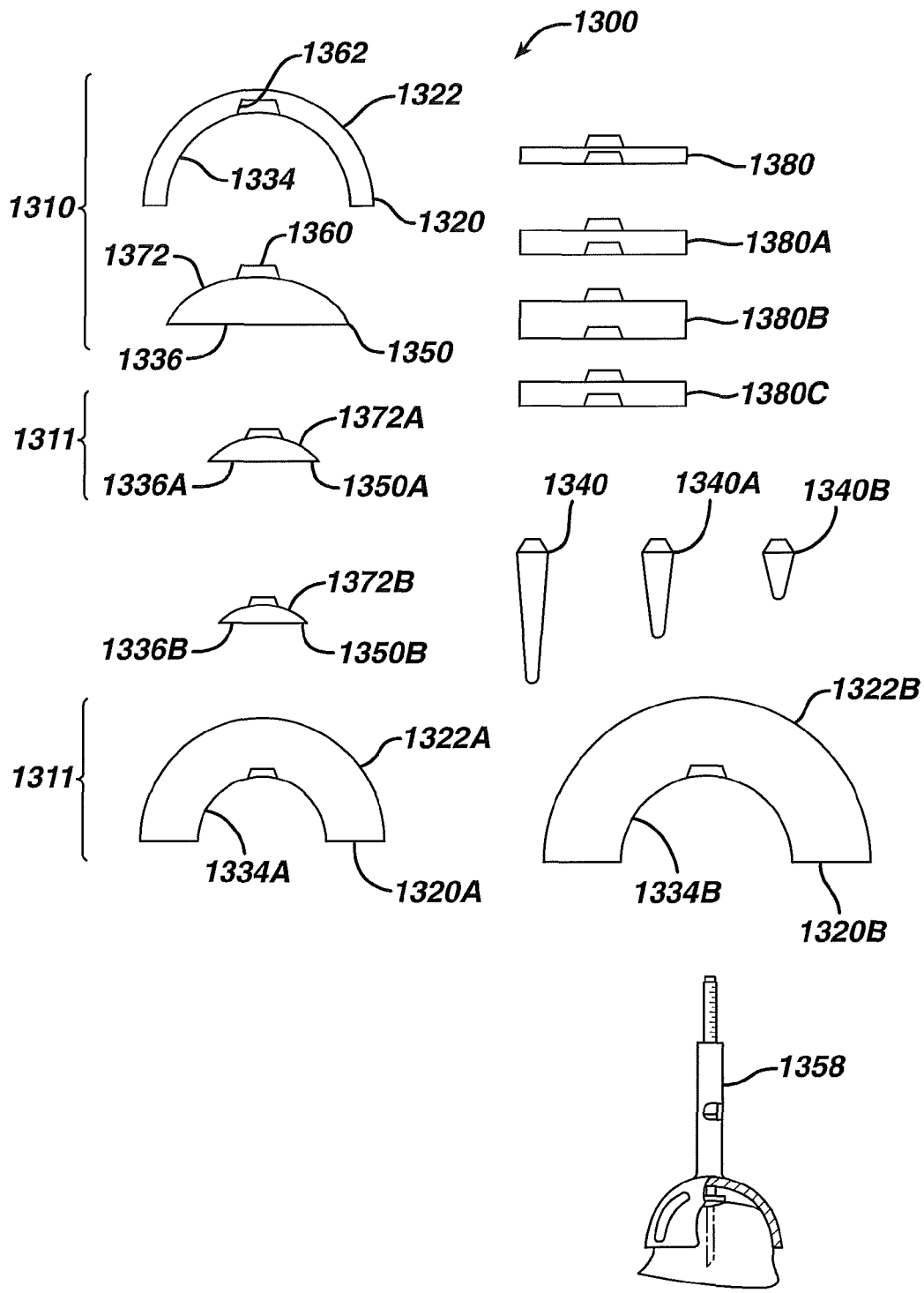
FIG. 26 is a plan view of a kit including a plurality of cups, liners, stems, and spacers for use in performing shoulder arthroplasty according to a further embodiment of the present disclosure.

Referring now to FIG. 26, another embodiment of the present invention in the form of kit 1300 is shown. Kit 1300 is similar to kit 1200 of FIG. 25 but includes additional components so that patients with greatly varying humeral sizes as well as varying conditions of the flattening of the humeral head, may be accommodated within the kit 1300. For example, as shown in FIG. 26, the kit 1300 includes a plurality of cups, plugs, spacers and stems so that a wide variety of patient humeral conditions can be accommodated.

As shown in FIG. 26, the kit 1300 includes a first cup 1320 having a first size articulating surface 1322. The kit 1300 also includes a second cup 1320A. The cup 1320A includes an articulating surface 1322A which is larger than the articulating surface 1322. The kit 1300 may also include a third cup 1320B, having an articulating surface 1322B, which is larger than the articulating surface 1322A of the cup 1320A.

So that the cups 1320, 1320A and 1320B may be utilized with common spacers, plugs and stems, preferably and as shown in FIG. 26, the cup 1320 has an internal arcuate surface 1334 which is the same size and shape as the articulating surface 1334A of the cup 1320A which is also the same size and shape as articulating inner surface 1334B of the cup 1320B.

The kit 1300 further includes a first plug 1350 having a planar surface 1336 and an opposed arcuate surface 1372. The arcuate surface 1372 of the first plug 1350 matingly fits against the arcuate surface 1334 of the first cup 1320. The kit 1300 further includes a second plug 1350A as well as a third plug 1350B.

The first plug 1350, the second plug 1350A and the third plug 1350B preferably each have a respective arcuate periphery 1372, 1372A and 1372B which all matingly fit with the arcuate surface 1334 of the cup 1320. Thus, the first plug 1350, the second plug 1350A and the third plug 1350B may be selectively mated with the first cup 1320. The first plug 1350, the second plug 1350A and the third plug 1350B each have a respective support surface 1336, 1336A and 1336B which provide for varying amounts of resection of the humerus 12.

The kit 1300 further includes a first spacer 1380, a second spacer 1380A, a third spacer 1380B and a fourth spacer 1380C. Each of the spacers 1380, 1380A, 1380B and 1380C have different thicknesses to accommodate a different amount of resection of the humerus 12.

The kit 1300 may further include a plurality of stems, for example, a first stem 1340, a second stem 1340A, and a third stem 1340B. Each of the stems 1340, 1340A and 1340B have a different length to accommodate a different size humerus. Preferably, and as shown in FIG. 26, for the components of the kit 1300 to be able to be easily matched, the components have external tapers 1360 which are all identical as well as internal tapers 1362 which are all identical, so that any internal taper 1362 may fit against an external taper 1360.

For example, as shown in FIG. 26, the cup 1320 may be combined with the plug 1350 to form a first prosthetic member 1310 and the second plug 1350A may be combined with the second cup 1320A to form a second prosthetic member 1311.

The kit 1300 may further include instruments 1358 to be used in conjunction with installing and removing the prosthesis.

Referring now to FIG. 27, a method for performing arthroplasty on the head of a long bone is shown as method 1400. Method 1400 includes first step 1402 of providing a reamer having a first cutting surface to prepare a convex support surface on the head of the long bone and having a second cutting surface to prepare a cavity in the head of the long bone. The method 1400 includes a second step 1404 of providing a prosthesis to resurface a portion of the head of the long bone, the prosthesis having a concave support surface and a stem. The method 1402 includes a third step 1406 of preparing the head of the long bone with a reamer to simultaneously prepare the convex support surface on the head of the long bone and the cavity in the head of the long bone. The method 1400 further includes a fourth step 1408 of implanting the prosthesis in the head of the long bone.

Figure 28:
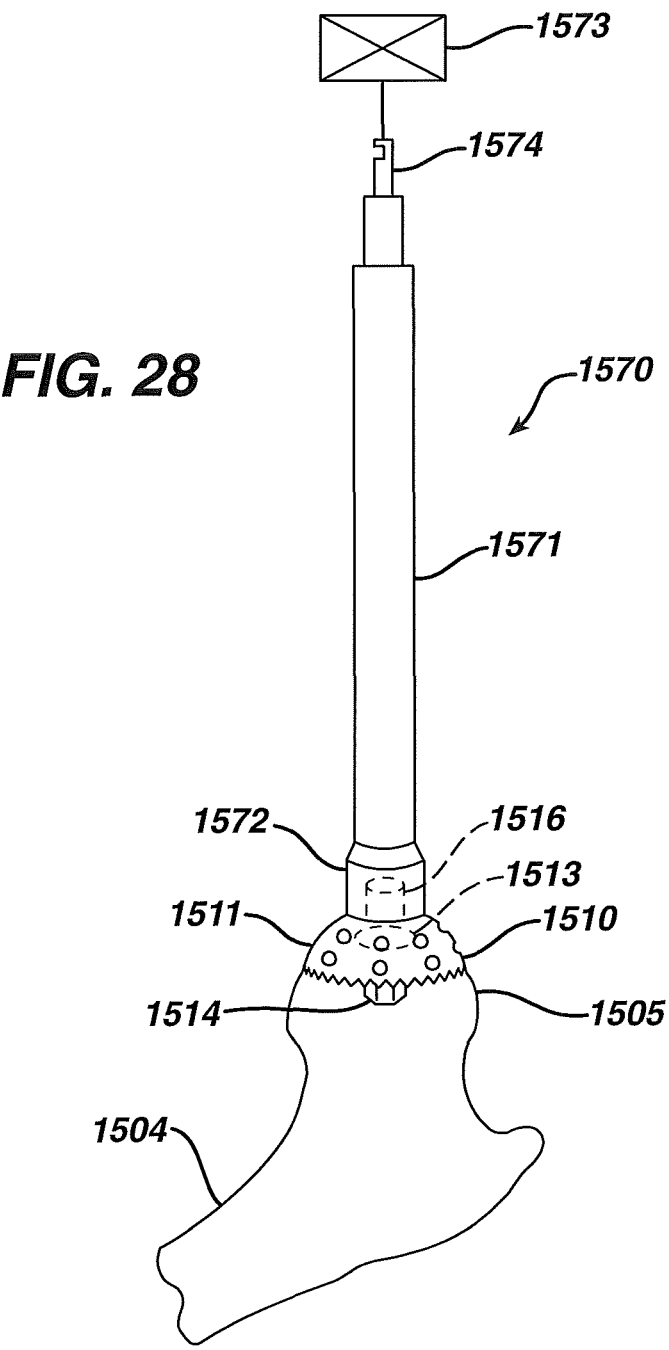
FIG. 28 is a perspective view of a reamer installed in a reamer assembly tool shown in position on a femur according to another embodiment of the present disclosure.

Referring now to FIG. 28, and according to another embodiment of the present invention, a cutting tool assembly 1570 is shown. The cutting tool assembly 1570 is similar to the cutting tool assembly 70 of FIG. 8 except the cutting tool assembly 1570 is designed to be used on the femoral head 1505 of femur 1504. The cutting tool assembly 1570 is shown in position against femoral head 1505 of femur 1504. The cutting tool assembly 1570 is utilized to perform arthroplasty, for example, a conservative or bone sparing arthroplasty to the head of the femur 1504.

The cutting tool assembly 1570 includes an instrument or cutting tool in the form of a reamer 1510. The reamer 1510 includes a first portion 1511 adapted to prepare a convex surface, a second portion 1513 adapted to prepare a planar surface, and a third portion 1514 adapted to prepare an elongated cavity. The reamer 1510 may also include a shank 1516 to be used to rotate the reamer 1510.

The cutting tool assembly 1570 further includes a driver or tool holder 1571. The driver 1571 is releasably securable to the reamer 1510. For example, the driver 1571 includes a tool-releasing adapter 1572 that is used to release the reamer 1510 from the driver 1571. Any standard available tool-releasing adapter 1572 may be utilized. As shown in FIG. 28, the driver 1571 is adapted to be attachable to a power tool 1573 to rotate the reamer 1510. The power tool 1573 may, for example, be a magnetic rotational tool, an electric rotational tool, or a hydraulic rotational tool, all commercially available. A driver adapter 1574 may be utilized to attach the driver 1571 to the power tool 1573.

Although the present invention and its advantages have been described in detail, it should be understood that various changes, substitutions, and alterations can be made therein without departing from the spirit and scope of the present invention as defined by the appended claims.

What is claimed is:

1. A reamer for use in performing arthroplasty, the reamer comprising:
    a first cutting structure having an inner concave surface that defines a first cavity and terminates distally in a generally circular leading edge, the inner concave surface including a first cutting feature that is spaced apart from the leading edge;
    an elongate member extending from the inner concave surface through the first cavity and toward the leading edge, the elongate member including a second cutting feature, the second cutting feature being located at least partially within the first cavity; and
    a second cutting structure secured to said elongate member and positioned within the first cavity, the second cutting structure extending outwardly from the elongate member toward the inner concave surface and including a third cutting feature,
    wherein the first cutting feature comprises a plurality of openings defined in the first cutting structure that extend through the inner concave surface, each of the openings having a cutting edge.

2. The reamer of claim 1, wherein the first cutting structure has a generally hemispherical shape.

3. The reamer of claim 1, wherein the leading edge of the first cutting structure comprises a cutting edge.

4. The reamer of claim 3, wherein the leading edge includes a plurality of cutting teeth.

5. The reamer of claim 1, wherein the elongate member is tapered.

6. The reamer of claim 1, wherein the second cutting feature comprises a plurality of flutes.

7. The reamer of claim 1, wherein the elongate member is cannulated.

8. The reamer of claim 1, wherein the second cutting structure comprises at least one cutting blade that extends outwardly from the elongate member.

9. The reamer of claim 8, wherein the second cutting structure comprises a plurality of cutting blades that evenly spaced apart from each other around a circumference of the elongate member.

10. The reamer of claim 8, wherein the plurality of cutting blades are cantilevered from the elongate member.

11. The reamer of claim 8, wherein the second cutting structure is fixed to the elongate member, and wherein the elongate member is removably attached to the first cutting structure.

12. A reamer for use in performing arthroplasty, the reamer comprising:
    a first cutting structure having an inner concave surface that defines a first cavity and terminates distally in a generally circular leading edge, the leading edge including a first cutting feature;
    an elongate member extending from the first cutting structure into the first cavity and toward the leading edge, the elongate member including a second cutting feature, the second cutting feature being located at least partially within the first cavity; and
    a second cutting structure secured to said elongate member and positioned within the first cavity, the second cutting structure extending outwardly from the elongate member toward the inner concave surface and including a third cutting feature,
    wherein the first cutting structure includes a plurality of openings that are spaced apart from the leading edge and that extend through the inner concave surface, each of the openings having a cutting edge.

13. The reamer of claim 12, wherein the leading edge includes a plurality of cutting teeth.

14. The reamer of claim 12, wherein the second cutting feature comprises a plurality of flutes.

15. A reamer for use in performing arthroplasty, the reamer comprising:
    a first cutting structure having an inner concave surface that defines a first cavity and terminates distally in a generally circular leading edge, the leading edge including a first cutting feature;
    an elongate member extending from the first cutting structure into the first cavity and toward the leading edge, the elongate member including a second cutting feature, the second cutting feature being located at least partially within the first cavity; and
    a second cutting structure secured to said elongate member and positioned within the first cavity, the second cutting structure extending outwardly from the elongate member toward the inner concave surface and including a third cutting feature,
    wherein the second cutting structure comprises at least one cutting blade that extends outwardly from the elongate member.

16. The reamer of claim 15, wherein the second cutting structure comprises a plurality of cutting blades that evenly spaced apart from each other around a circumference of the elongate member.

17. The reamer of claim 15, wherein the plurality of cutting blades are cantilevered from the elongate member.

18. A reamer for use in performing arthroplasty, the reamer comprising:
    a first cutting structure having an inner concave surface that defines a first cavity and terminates distally in a generally circular leading edge, the leading edge including a first cutting feature;
    an elongate member extending from the first cutting structure into the first cavity and toward the leading edge, the elongate member including a second cutting feature, the second cutting feature being located at least partially within the first cavity; and
    a second cutting structure secured to said elongate member and positioned within the first cavity, the second cutting structure extending outwardly from the elongate member toward the inner concave surface and including a third cutting feature,
    wherein the second cutting structure is fixed to the elongate member, and wherein the elongate member is removably attached to the first cutting structure.

* * * * *